US012679889B2

(12) United States Patent　　　　　(10) Patent No.:　US 12,679,889 B2
Konrad et al.　　　　　　　　　　　　(45) Date of Patent:　　Jul. 14, 2026

(54) OXYNTOMODULIN BINDING MOLECULES, AND USES THEREOF

(71) Applicant: Eli Lilly and Company, Indianapolis, IN (US)

(72) Inventors: Robert John Konrad, Carmel, IN (US); Wenyu Ming, Carmel, IN (US); Robert William Siegel, II, Fountaintown, IN (US); Tara Suzanne Umberger, Frankton, IN (US)

(73) Assignee: Eli Lilly and Company, Indianapolis, IN (US)

( * ) Notice: Subject to any disclaimer, the term of this patent is extended or adjusted under 35 U.S.C. 154(b) by 469 days.

(21) Appl. No.: 18/259,892

(22) PCT Filed: Jan. 19, 2022

(86) PCT No.: PCT/US2022/012898
§ 371 (c)(1),
(2) Date: Jun. 29, 2023

(87) PCT Pub. No.: WO2022/159437
PCT Pub. Date: Jul. 28, 2022

(65) Prior Publication Data
US 2024/0059770 A1　　Feb. 22, 2024

Related U.S. Application Data

(60) Provisional application No. 63/139,428, filed on Jan. 20, 2021.

(51) Int. Cl.
*C07K 16/28*　　　(2006.01)
*C07K 16/26*　　　(2006.01)
*C12N 15/63*　　　(2006.01)
*G01N 33/68*　　　(2006.01)
*G01N 33/74*　　　(2006.01)

(52) U.S. Cl.
CPC .............. *C07K 16/26* (2013.01); *C12N 15/63* (2013.01); *G01N 33/74* (2013.01); *C07K 2317/14* (2013.01); *C07K 2317/565* (2013.01); *G01N 2800/50* (2013.01)

(58) Field of Classification Search
None
See application file for complete search history.

(56) References Cited

U.S. PATENT DOCUMENTS 9,453,073 B2 * 9/2016 Watson ................. C07K 16/26
2016/0075778 A1 3/2016 Okamoto

FOREIGN PATENT DOCUMENTS

WO　　2013/081993 A1　6/2013

OTHER PUBLICATIONS

Albrechtsen et al. (2016) EBioMedicine 7: 112-120.*
Albrechtsen NJW. (2017) Danish Medical Journal 64(11): B5425, 1-16.*
Pendharkar et al. (2019) Horm Metab Res 51: 191-199.*
Bharmal et al. (2020) Clin. Transl. Gastroenterology 11:e00132, 1-12.*
Bharmal et al. (2022) Pancreas 51: 774-783.*
Umberger et al. (2022) Bioanalysis 14(18), 1229-1239.*
Bak, et al., "Specificity and sensitivity of commercially available assays for glucagon and oxyntomodulin measurement in humans", European Journal of Endocrinology, vol. 170, No. 4, Apr. 1, 2014, pp. 529-538.
Bataille, et al., The biological significance of 'Enteroglucagon', Peptides, Elsevier, Amsterdam, NL, vol. 7, Jan. 1, 1986, pp. 37-42.
Wewer, et al., "Hyperglucagonaemia analysed by glucagon sandwich ELISA: nonspecific interference or truly elevated levels?", Diabetologia, vol. 57, No. 9, Sep. 1, 2014, pp. 1919-1926.

* cited by examiner

*Primary Examiner* — Ilia I Ouspenski
(74) *Attorney, Agent, or Firm* — Duane C. Marks

(57) ABSTRACT

Provided herein are novel N- and C-terminal oxyntomodulin polypeptide binding molecules, and uses thereof, including a method for quantitating oxyntomodulin.

26 Claims, No Drawings
Specification includes a Sequence Listing.

OXYNTOMODULIN BINDING MOLECULES, AND USES THEREOF

Oxyntomodulin is a proglucagon-derived peptide agonist of both the glucagon-like peptide-1 (GLP-1) and glucagon receptors, and is a key regulator of gastric acid secretion and energy expenditure. Oxyntomodulin is a potential target for therapeutic intervention (Pocai A, *Mol. Metab.* 2014; 3:241-51), and has been proposed as a potential biomarker for predicting if a subject is at risk of developing type 2 diabetes after acute pancreatitis (Bharmal, S H, et al., *Clin. Transl. Gastroenterology* 2020; 11: page e00132, doi: 10.14309/ctg.00000000 00000132).

Human proglucagon is cleaved into a number of different peptides in a tissue-specific manner (Holst J J, et al., *Peptides* 2018; 100: 48-53), and sequence similarities between proglucagon cleavage peptides have made the quantitation of endogenous levels of oxyntomodulin difficult. Historically, polyclonal antibodies directed to specific regions of glucagon (33-61) or the C-terminal octapeptide (62-69) have been used to quantitate oxyntomodulin-like immunoreactive (OLI) components in various tissues and plasma. Initially, a two-step subtractive radioimmunoassay was used to estimate OLI after the specific subtraction of pancreatic glucagon levels (Kervran A, et al., *Endocrinology* 1987; 121:704-1). Subsequent assays used polyclonal antibodies directed to the C-terminal octapeptide to directly measure OLI components (Blache P, et al., *Anal Biochem* 1988; 173:151-9; Collie N L, et al., *Proc Natl Acad Sci USA* 1994; 91:9362-6; Le Quellec A, et al., *J. Clin. Endocrinol. Metab* 1992; 74:1405), and assays based on that approach are now commercially available.

Nonetheless, estimates of endogenous OLI in human plasma vary widely from 60 to 5000 ng/L in the fasted state (Laferrere B, et al., *J. Clin. Endocrinol. Metab.* 2010; 95:4072-6; Le Quellec A, et al., *J. Clin. Endocrinol. Metab* 1992; 74:1405-9). Furthermore, the proportion of OLI represented by glicentin confounds accurate oxyntomodulin quantification, and obscures the physiological role(s) of oxyntomodulin (Bak M J, et al., *Eur. J. Endocrinol.* 2014; 170:529-3). Oxyntomodulin can be distinguished from glicentin using HPLC or LC-MS, but those approaches lack sufficient analytical sensitivity to quantitate endogenous levels of oxyntomodulin in plasma (Lee A Y, et al., *Clin. Chem.* 2015; 62: 227-235). A sandwich assay has been reported (Albrechtsen, N J, et al., *EBioMedicine* 2016; 7: 112-120), but it lacks specificity, because it is characterized by 10% cross-reactivity with glicentin (Holst J J, el al., *Peptides* 2018, 100: 48-53).

Thus, decades after the discovery of oxyntomodulin, the research community has been unable to selectively and reliably measure endogenous levels of oxyntomodulin in human plasma samples, and there remains a need for an assay that is not only selective and sensitive, but that is also amendable to high throughput application.

A sandwich immunoassay is an assay that utilizes two antibodies that bind to different sites on an antigen of interest. However, to implement an oxyntomodulin sandwich immunoassay, antibodies are required that (a) bind distinct epitopes of respective proglucagon fragments, and (b) detect oxyntomodulin only when used together in the assay. The present invention provides antibodies and methods that facilitate a sandwich assay method for quantitating oxyntomodulin and a predictive method for determining if a subject is at risk of developing diabetes.

The present invention provides a polypeptide molecule that binds the N-terminal region of each of human oxyntomodulin (SEQ ID NO: 25) and human glucagon (SEQ ID NO: 30), wherein the polypeptide molecule comprises the complementarity determining regions (CDRs) set forth in SEQ ID NOS: 1-6. In one embodiment, the polypeptide molecule is an antibody. In another embodiment, the polypeptide molecule is an antibody fragment, wherein the antibody fragment binds the N-terminal region of each of human oxyntomodulin (SEQ ID NO: 25) and human glucagon (SEQ ID NO: 30) and comprises SEQ ID NOS: 1-6. In another embodiment, the antibody fragment is an scFv. In another embodiment, the antibody fragment is a Fab.

In another embodiment, the polypeptide molecule is an antibody comprising a heavy chain variable region (HCVR or VH) comprising SEQ ID NO: 7 and a light chain variable region (LCVR or VL) comprising SEQ ID NO: 8. In another embodiment, the polypeptide molecule is an antibody comprising a heavy chain comprising SEQ ID NO: 9 and a light chain comprising SEQ ID NO: 10. In another embodiment, the polypeptide molecule is an antibody comprising a heavy chain consisting of a SEQ ID NO: 9 and a light chain consisting of SEQ ID NO: 10. The present invention also provides a composition comprising the polypeptide molecule.

The present invention also provides a nucleic acid molecule comprising one or both of a first nucleic acid sequence encoding SEQ ID NO: 9 and a second nucleic acid sequence encoding SEQ ID NO: 10. In another embodiment, the first nucleic acid sequence encoding SEQ ID NO: 9 comprises the nucleic acid of SEQ ID NO: 11, and the second nucleic acid sequence encoding SEQ ID NO: 10 comprises the nucleic acid of SEQ ID NO: 12. The present invention also provides a vector comprising one or both of a first nucleic acid sequence encoding SEQ ID NO: 9 and a second nucleic acid sequence encoding SEQ ID NO: 10. The present invention also provides a composition comprising the vector. The present invention also provides a cell comprising the vector. In one embodiment, the cell is a mammalian cell. The present invention also provides a process of producing a polypeptide molecule, comprising culturing the cell under conditions such that the polypeptide molecule is expressed, and recovering the expressed polypeptide molecule from the culture medium. The present invention also provides a polypeptide molecule produced by the process.

The present invention also provides a polypeptide molecule that binds the C-terminal region of each of human oxyntomodulin (SEQ ID NO: 25) and human glicentin (SEQ ID NO: 28), wherein the polypeptide molecule comprises the complementarity determining regions set forth in SEQ ID NOS: 13-18. In one embodiment, the polypeptide molecule is an antibody. In another embodiment, the polypeptide molecule is a fragment of the antibody, wherein the fragment binds the C-terminal region of each of human oxyntomodulin (SEQ ID NO: 25) and human glicentin (SEQ ID NO: 28). In another embodiment, the fragment of the polypeptide molecule is an scFv. In another embodiment, the fragment of the polypeptide molecule is a Fab.

In another embodiment, the polypeptide molecule is an antibody comprising a VH comprising SEQ ID NO: 19 and a VL comprising SEQ ID NO: 20. In another embodiment, the polypeptide molecule is an antibody comprising a heavy chain comprising SEQ ID NO: 21 and a light chain comprising SEQ ID NO: 22. In another embodiment, the polypeptide molecule is an antibody comprising a heavy chain consisting of a SEQ ID NO:21 and a light chain consisting of SEQ ID NO: 22. The present invention also provides a composition comprising the polypeptide molecule.

The present invention also provides a nucleic acid molecule comprising one or both of a first nucleic acid sequence encoding SEQ ID NO: 21 and a second nucleic acid sequence encoding SEQ ID NO: 22. In one embodiment, the first nucleic acid sequence encoding SEQ ID NO: 21 comprises the nucleic acid of SEQ ID NO: 23, and the second nucleic acid sequence encoding SEQ ID NO: 22 comprises the nucleic acid of SEQ ID NO: 24. The present invention also provides a vector comprising one or both of a first nucleic acid sequence encoding SEQ ID NO: 23 and a second nucleic acid sequence encoding SEQ ID NO: 24. The present invention also provides a composition comprising the vector. The present invention also provides a cell comprising the vector. In one embodiment, the cell is a mammalian cell. The present invention also provides a process of producing a polypeptide molecule, comprising culturing the cell under conditions such that the polypeptide molecule is expressed, and recovering the expressed polypeptide molecule from the culture medium. The present invention also provides a polypeptide molecule produced by the process.

The present invention also provides a composition comprising (a) a first polypeptide molecule that binds the N-terminal region of each of human oxyntomodulin (SEQ ID NO: 25) and human glucagon (SEQ ID NO: 30), wherein the first polypeptide molecule comprises SEQ ID NOS: 1-6, and (b) a second polypeptide molecule that binds the C-terminal region of each of human oxyntomodulin (SEQ ID NO: 25) and human glicentin (SEQ ID NO: 28), wherein second the polypeptide molecule comprises SEQ ID NOS: 13-18.

The present invention also provides a sandwich assay method for determining the amount of human oxyntomodulin (SEQ ID NO: 25) in a liquid sample, comprising: (a) contacting a liquid sample comprising human oxyntomodulin with a first polypeptide molecule that binds the C-terminal region of each of human oxyntomodulin (SEQ ID NO: 25) and human glicentin (SEQ ID NO: 28), wherein the first polypeptide molecule comprises SEQ ID NOS: 13-18, thereby forming a first polypeptide molecule-human oxyntomodulin complex; (b) contacting a second polypeptide molecule that binds the N-terminal region of each of human oxyntomodulin (SEQ ID NO: 25) and human glucagon (SEQ ID NO: 30), wherein the second polypeptide molecule comprises SEQ ID NOS: 1-6, thereby forming a first polypeptide molecule-human oxyntomodulin-second polypeptide molecule complex; and (c) quantitating the amount of oxyntomodulin in the first polypeptide molecule-human oxyntomodulin-second polypeptide molecule complex by comparison against a standard curve of known amounts of human oxyntomodulin (SEQ ID NO: 25).

In another embodiment of the methods of the invention, the first polypeptide molecule is an antibody and the second polypeptide molecule is an antibody. In another embodiment, the first polypeptide molecule is an antibody comprising a VH comprising SEQ ID NO: 19 and a VL comprising SEQ ID NO: 20, and the second polypeptide molecule is an antibody comprising a VH comprising SEQ ID NO: 7 and a VL comprising SEQ ID NO: 8. In another embodiment, the first polypeptide molecule is an antibody comprising a heavy chain comprising SEQ ID NO: 21 and comprising a light chain comprising SEQ ID NO: 22, and the second polypeptide molecule is an antibody comprising a heavy chain comprising SEQ ID NO: 9 and a light chain comprising SEQ ID NO: 10. In another embodiment, the first polypeptide molecule is an antibody comprising a heavy chain consisting of SEQ ID NO: 21 and comprising a light chain consisting of SEQ ID NO: 22, and the second polypeptide molecule is an antibody comprising a heavy chain consisting of SEQ ID NO: 9 and a light chain consisting of SEQ ID NO: 10.

The present invention also provides a method of predicting if a subject is at risk of developing type 2 diabetes, comprising determining the centration of oxyntomodulin in a serum sample or a plasma sample from a subject, comprising: (a) contacting a serum sample or a plasma sample comprising human oxyntomodulin with a first polypeptide molecule that binds the C-terminal of each of human oxyntomodulin (SEQ ID NO: 25) and human glicentin (SEQ ID NO: 28), wherein the first polypeptide molecule comprises SEQ ID NOS: 13-18, thereby forming a first polypeptide molecule-human oxyntomodulin complex; (b) contacting a second polypeptide molecule that binds the N-terminal region of each of human oxyntomodulin (SEQ ID NO: 25) and human glucagon (SEQ ID NO: 30), wherein the second polypeptide molecule comprises SEQ ID NOS: 1-6, thereby forming a first polypeptide molecule-human oxyntomodulin-second polypeptide molecule complex; and (c) quantitating the amount of oxyntomodulin in the first polypeptide molecule-human oxyntomodulin-second polypeptide molecule complex by comparison against a standard curve of known amounts of human oxyntomodulin (SEQ ID NO: 25). In one embodiment of the method, the subject has been diagnosed with acute pancreatitis.

The present invention also provides the use of a first polypeptide molecule that binds the C-terminal octapeptide present in each of human oxyntomodulin (SEQ ID NO: 25) and human glicentin (SEQ ID NO: 28), and a second polypeptide molecule that binds the N-terminal region of each of human oxyntomodulin (SEQ ID NO: 25) and human glucagon (SEQ ID NO: 30), in determining the concentration of oxyntomodulin in a liquid sample.

In one embodiment of the methods of the invention, the liquid sample is serum. In another embodiment, the liquid sample is plasma.

In the methods of the invention, the first polypeptide molecule can be attached to a solid support. In one embodiment, the solid surface is a plate. In another embodiment, the solid surface is a plurality of beads. Such solid supports include, e.g., without limitation, glass, cellulose, plastic, poly-acrylamide, nylon, polystyrene, polyvinyl chloride, or polypropylene.

In another embodiment of the methods of the invention, the first polypeptide molecule is attached directly to the solid surface. In another embodiment, the first polypeptide molecule is indirectly attached to the solid surface with an attachment agent. In one embodiment, the attachment agent is streptavidin, neutravidin or avidin that is coated on the solid surface, and the polypeptide molecule is biotinylated.

In another embodiment of the methods of the invention, prior to contacting the liquid sample with the first polypeptide molecule, the solid surface is contacted with a blocking solution. In another embodiment, after contacting the liquid sample with the first polypeptide molecule, the first polypeptide molecule-human oxyntomodulin complex is contacted with a wash solution, thereby removing uncomplexed human oxyntomodulin.

In another embodiment of the methods of the invention, the first polypeptide molecule-human oxyntomodulin-second polypeptide molecule complex is contacted with a wash solution, thereby removing uncomplexed second polypeptide molecule.

In another embodiment of the method of determining the amount of human oxyntomodulin (SEQ ID NO: 25) in a liquid sample, e.g., plasma, the method comprises:

(a) contacting a solid surface, to which an antibody comprising a heavy chain comprising SEQ ID NO: 21 and a light chain comprising SEQ ID NO: 22 is attached, with a blocking solution;

(b) contacting a liquid sample comprising human oxyntomodulin with a first antibody comprising a heavy chain comprising SEQ ID NO: 21 and a light chain comprising SEQ ID NO: 22 attached to a solid surface, thereby forming a first antibody-human oxyntomodulin complex;

(c) contacting the solid surface with a wash solution, thereby removing uncomplexed human oxyntomodulin;

(d) contacting the solid surface with a second antibody comprising a heavy chain comprising SEQ ID NO: 9 and a light chain comprising SEQ ID NO: 10, thereby forming a first antibody-human oxyntomodulin-second antibody complex;

(e) contacting the solid surface with a wash solution, thereby removing uncomplexed second antibody; and (f) quantitating the amount of oxyntomodulin in the first antibody-human oxyntomodulin-second antibody complex by comparison against a standard curve of known amounts of human oxyntomodulin (SEQ ID NO: 25).

In another embodiment of the predictive method of the invention, the method comprises:

(a) contacting a solid surface, to which an antibody comprising a heavy chain comprising SEQ ID NO: 21 and a light chain comprising SEQ ID NO: 22 is attached, with a blocking solution;

(b) contacting a liquid sample comprising human oxyntomodulin with a first antibody comprising a heavy chain comprising SEQ ID NO: 21 and a light chain comprising SEQ ID NO: 22 attached to a solid surface, thereby forming a first antibody-human oxyntomodulin complex;

(c) contacting the solid surface with a wash solution, thereby removing uncomplexed human oxyntomodulin;

(d) contacting the solid surface with a second antibody comprising a heavy chain comprising SEQ ID NO: 9 and a light chain comprising SEQ ID NO: 10, thereby forming a first antibody-human oxyntomodulin-second antibody complex;

(e) contacting the solid surface with a wash solution, thereby removing uncomplexed second antibody; and (f) quantitating the amount of oxyntomodulin in the first antibody-human oxyntomodulin-second antibody complex by comparison against a standard curve of known amounts of human oxyntomodulin (SEQ ID NO: 25).

In another embodiment of the methods of the invention, the second polypeptide molecule is labeled. In another embodiment, quantification of the amount of second polypeptide is performed by quantitating the label. In another embodiment, the label is a radiolabel. In another embodiment, the radiolabel is ruthenium.

The polypeptide molecules, methods and uses of the invention facilitate quantifying oxyntomodulin that is selective and sensitive. In one embodiment, the method results in one or more of: a lower limit of oxyntomodulin quantitation (LLOQ) of 0.4 ng/L, no detection of glucagon, and/or less than 0.5% cross-reactivity with glicentin. An additional benefit of the method of the invention is that it facilitates quantitation of the pre- and post-meal levels of oxyntomodulin, with results that are highly correlated with results obtained using a conventional orthogonal IA-LC-MS assay.

Human proglucagon (SEQ ID NO: 36) contains 180 amino acid residues, and is encoded by the GCG gene (GCG-Pro-glucagon precursor-*Homo sapiens* (Human)-GCG gene & protein, unprot.org/uniprot/P01275 #sequences (2007)). This polypeptide precursor is differentially cleaved into a number of different peptides in a tissue-specific manner to generate a panel of peptides with different biological activities: a signal peptide (amino acid residues 1-20); human glicentin (amino acid residues 21-89); human glicentin-related pancreatic polypeptide (amino acid residues 21-50); human oxyntomodulin (amino acid residues 53-89); human glucagon (amino acid residues 53-81); human glucagon-like peptide 1 (GLP-1) (amino acid residues 92-128); human GLP-1 (7-37) (amino acid residues 98-128); human GLP-1 (7-36) (amino acid residues 98-127); and human glucagon-like peptide 2 (GLP-2) (amino acid residues 146-178). One outcome of the tissue-specific cleavage patterns from a common polypeptide precursor (SEQ ID 36) is the generation of biologically active peptides that have some sequence overlaps. For example, human oxyntomodulin (amino acid residues 53-89) contains all the sequences contained in human glucagon (amino acid residues 53-81) in addition to 8 amino acids that extend past amino acid residue 81. As another example, the sequences present in human oxyntomodulin (amino acid residues 53-89) and human glucagon (amino acid residues 53-81) are also contained in human glicentin (amino acid residues 21-89); however, human glicentin (amino acid residues 21-89) contains an additional 32 amino acids that precede residue 53 in both human oxyntomodulin (amino acid residues 53-89) and human glucagon (amino acid residues 53-81).

Sequences referred to herein are set forth in Table 1. The parenthetical numberings in certain sequence names in Table 1 refer to the respective amino acid residues in human proglucagon that includes the signal peptide sequence (residues 1-20). For example, in the term, "human oxyntomodulin (53-89)," the term "(53-89)" refers to amino acid residues 53-89 in human proglucagon. A deletion version of a human sequence in Table 1 is provided without the term "human." For example, the term "oxyntomodulin (55-89)" refers to a human oxyntomodulin fragment with sequence that corresponds to amino acid residues 55-59 of human proglucagon, and that does not contain the first two N-terminal amino acid residues found in human oxyntomodulin.

TABLE 1

| Sequences | | |
|---|---|---|
| Name | | SEQ ID NO: |
| Anti-Human Oxyntomodulin N-Terminal Antibody | HCDR1 (amino acid (AA)) | 1 |
| | HCDR2 (AA) | 2 |
| | HCDR3 (AA) | 3 |
| | LCDR1 (AA) | 4 |
| | LCDR2 (AA) | 5 |
| | LCDR3 (AA) | 6 |
| | Variable heavy region (VH) (AA) | 7 |
| | Variable light region (VL) (AA) | 8 |
| | Heavy chain (AA) | 9 |
| | Light chain (AA) | 10 |
| | Heavy Chain (DNA) | 11 |
| | Light Chain (DNA) | 12 |
| Anti-Human Oxyntomodulin C-Terminal Antibody | HCDR1 (AA) | 13 |
| | HCDR2 (AA) | 14 |
| | HCDR3 (AA) | 15 |
| | LCDR1 (AA) | 16 |
| | LCDR2 (AA) | 17 |
| | LCDR3 (AA) | 18 |
| | Variable heavy region (VH) (AA) | 19 |

TABLE 1-continued

| Sequences | |
|---|---|
| Name | SEQ ID NO: |
| Variable light region (CL) (AA) | 20 |
| Heavy chain (AA) | 21 |
| Light chain (AA) | 22 |
| Heavy Chain (DNA) | 23 |
| Light Chain (DNA) | 24 |
| human oxyntomodulin (53-89) | 25 |
| oxyntomodulin (55-89) | 26 |
| oxyntomodulin (56-89) | 27 |
| human glicentin (21-89) | 28 |
| glicentin span (49-89) | 29 |
| human glucagon (53-81) | 30 |
| glucagon (55-81) | 31 |
| glucagon (56-61) | 32 |
| human glucose-dependent insulinotrophic polypeptide (GIP) | 33 |
| GLP-1 (98-128) | 34 |
| GLP-1 (100-128) | 35 |
| Human proglucagon (1-180) | 36 |

The term "N-terminal region of each of human glucagon and human oxyntomodulin" as used herein refers to the first three amino acid residues in each of those peptides, in which an N-terminal histidine is present.

The term "binds the N-terminal region of each of human glucagon and human oxyntomodulin" as used herein refers to (a) binding to each of human oxyntomodulin (53-59) (SEQ ID NO: 25) and human glucagon (SEQ ID NO: 30), each of which have an N-terminal histidine residue, (b) does not bind to oxyntomodulin (55-89) or oxyntomodulin (56-89), because oxyntomodulin (55-89) and oxyntomodulin (56-89) do not contain the N-terminal histidine residue found in human oxyntomodulin (53-59) and human glucagon (SEQ ID NO: 30), and (c) does not bind to glicentin span (49-89) because although glicentin span (29-69) contains the histidine it is not present with a free amine terminus.

The term "C-terminal region of each of human oxyntomodulin (SEQ ID NO: 25) and human glicentin (SEQ ID NO: 28)" as used herein refers to amino acid residues 30-37 in human oxyntomodulin and amino acid residues 61-69 in human glicentin (SEQ ID NO: 28).

The term "binds the C-terminal region of each of human oxyntomodulin (SEQ ID NO: 25) and human glicentin (SEQ ID NO: 28)" as used herein refers to binding to one or more of amino acid residues 30-37 in human oxyntomodulin and one or more of amino acid residues 61-69 in human glicentin (SEQ ID NO: 28).

The term "N-Terminal Antibody" as used herein refers to the antibody having a heavy chain amino acid sequence of SEQ ID NO: 9 and a light chain amino acid sequence of SEQ ID NO: 10.

The term "C-Terminal Antibody" as used herein refers to the antibody having a heavy chain amino acid sequence of SEQ ID NO: 21 and a light chain amino acid sequence of SEQ ID NO: 22.

The term "polypeptide molecule" as used herein refers to a molecule that comprises a polymer of amino acid residues. In one embodiment, the polypeptide molecule consists of a polymer of amino acid residues.

The term "contacting" as used herein refers to the exposing a substance to another substance. For example, a sample can be exposed to a polypeptide molecule of the invention, for a time and under conditions that permit the polypeptide molecule to bind to human oxyntomodulin present in the sample. Such time and conditions are known to one of skill in the art, and/or can be routinely determined by methods known in the art according to references cited herein.

The term "complex" as used herein refers to the protein-protein interaction between, e.g., a polypeptide molecule and human oxyntomodulin (SEQ ID NO: 25). "First polypeptide molecule-human oxyntomodulin complex" as used herein refers to the protein-protein interaction between a molecule of a polypeptide molecule of the invention and a molecule of human oxyntomodulin (SEQ ID NO: 25). "First polypeptide molecule-human oxyntomodulin-second polypeptide molecule complex" as used herein refers to the concomitant protein-protein interaction between (a) a molecule of a first polypeptide molecule of the invention and a molecule of human oxyntomodulin (SEQ ID NO: 25), and (b) a molecule of a second polypeptide molecule of the invention and the same molecule of human oxyntomodulin molecule (SEQ ID NO: 25).

The term "quantitating the amount of oxyntomodulin" as used herein refers to measuring the amount of oxyntomodulin in a sample, e.g., a liquid sample. Suitable assays are known to those of ordinary skill in the art, such as ELISA.

A polypeptide molecule of the invention can be conjugated to an enzyme and used in an enzyme-linked immunosorbent assay (ELISA). Such assays are described in detail in, for example, Butler (1994) "ELISA" (Chapter 29), In: van Oss, C. J. et al., eds., Immunochemistry, Marcel Dekker, Inc., New York, pp. 759-803. The present polypeptide molecules can also be used in radioimmunoassay and fluorescence-activated cell sorting (FACS) analysis of oxyntomodulin expression.

A particular protein such as human oxyntomodulin can be measured by a variety of immunoassay methods including, e.g., without limitation, competitive and non-competitive assay systems using techniques such as, e.g., without limitation, Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays. For a review of immunological and immunoassay procedures in general, see for example Stites and Terr (eds.), Basic and Clinical Immunology (7th ed.) (1991). Moreover, immunoassays can be performed in many configurations as is known in the art (See for example Maggio (ed.), *Enzyme Immunoassay* CRC Press, Boca Raton, Florida (1980); Gosling J P, *Immunoassays: A Practical Approach* (Practical Approach Series), Oxford Univ Press (2000); Diamandis & Christopoulus, *Immunoassay*, Academic Press (San Diego, CA) (1996).

The term "antibody," as used herein, refers to an immunoglobulin molecule that binds an antigen. Embodiments of an antibody include a monoclonal antibody, polyclonal antibody, human antibody, humanized antibody, chimeric antibody, bispecific or multispecific antibody, or conjugated antibody. The antibodies can be of any class (e.g., IgG, IgE, IgM, IgD, IgA), and any subclass (e.g., IgG1, IgG2, IgG3, IgG4).

An exemplary antibody of the present disclosure is an immunoglobulin G (IgG) type antibody comprised of four polypeptide chains: two heavy chains (HC) and two light chains (LC) that are cross-linked via inter-chain disulfide bonds. The amino-terminal portion of each of the four polypeptide chains includes a variable region of about 100-125 or more amino acids primarily responsible for antigen recognition. The carboxyl-terminal portion of each of the four polypeptide chains contains a constant region primarily responsible for effector function. Each heavy chain is comprised of a heavy chain variable region (VH) and a heavy chain constant region. Each light chain is comprised of a light chain variable region (VL) and a light chain constant region. The IgG isotype may be further divided into subclasses (e.g., IgG1, IgG2, IgG3, and IgG4).

The VH and VL regions can be further subdivided into regions of hyper-variability, termed complementarity determining regions (CDRs), interspersed with regions that are more conserved, termed framework regions (FR). The CDRs are exposed on the surface of the protein and are important regions of the antibody for antigen binding specificity. Each VH and VL is composed of three CDRs and four FRs, arranged from amino-terminus to carboxyl-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues that form specific interactions with the antigen. Assignment of amino acid residues to the CDRs may be done according to the well-known schemes, including those described in Kabat (Kabat et al., "Sequences of Proteins of Immunological Interest," National Institutes of Health, Bethesda, Md. (1991)), Chothia (Chothia et al., "Canonical structures for the hypervariable regions of immunoglobulins", Journal of Molecular Biology, 196, 901-917 (1987); Al-Lazikani et al., "Standard conformations for the canonical structures of immunoglobulins", Journal of Molecular Biology, 273, 927-948 (1997)), North (North et al., "A New Clustering of Antibody CDR Loop Conformations", Journal of Molecular Biology, 406, 228-256 (2011)), or IMGT (the international ImMunoGeneTics database available on at www.imgt.org: see Lefranc et al., Nucleic Acids Res. 1999; 27:209-212).

An "antibody fragment" or "antigen-binding fragment" that, as used herein, comprise at least a portion of an antibody retaining the ability to specifically interact with an antigen or an epitope of the antigen, such as Fab, Fab', F(ab')$_2$, Fv fragments, scFv antibody fragments, scFab, disulfide-linked Fvs (sdFv), a Fd fragment.

The terms "bind" and "binds" as used herein are intended to mean, unless indicated otherwise, the ability of a protein or molecule to form a chemical bond or attractive interaction with another protein or molecule, which results in proximity of the two proteins or molecules as determined by common methods known in the art, for example, the molecular interaction between two molecules, e.g., a polypeptide molecule of the invention and, e.g., human oxyntomodulin (SEQ ID NO: 25). In one embodiment, a polypeptide molecule of the present invention binds specifically to human oxynto-modulin. In another embodiment, "specifically binds" means that a polypeptide molecule of the invention interacts more frequently, more rapidly, with greater duration, with greater affinity, or with some combination of the above to human oxyntomodulin. In another preferred embodiment, "specifically binds" means that a polypeptide molecule of the invention binds to human oxyntomodulin with a $K_D$ of about 0.1 mM or less. In another preferred embodiment, "specifically binds" means that a polypeptide molecule of the invention binds to human oxyntomodulin with a $K_D$ of about 0.01 mM or less. In another preferred embodiment, "specifically binds" means that a polypeptide molecule of the invention binds to human oxyntomodulin with a $K_D$ of about 0.001 mM or less. In another preferred embodiment, "specifically binds" means that a polypeptide molecule of the invention binds to human oxyntomodulin with a $K_D$ of about 0.0001 mM or less.

An isolated polynucleotide molecule encoding a HCVR region may be converted to a full-length heavy chain gene by operably linking the HCVR-encoding polynucleotide to another polynucleotide molecule encoding heavy chain constant regions. The sequences of human, as well as other mammalian, heavy chain constant region genes are known in the art. Polynucleotide fragments encompassing these regions may be obtained, e.g., by standard PCR amplification.

An isolated polynucleotide molecule encoding a LCVR region may be converted to a full-length light chain gene by operably linking the LCVR-encoding polynucleotide to another polynucleotide molecule encoding a light chain constant region. The sequences of human, as well as other mammalian, light chain constant region genes are known in the art. Polynucleotide fragments encompassing these regions may be obtained by standard PCR amplification.

The term "sensitivity" as used herein refers to the lowest level of an analyte (in this case, human oxyntomodulin) that can be measured with acceptable accuracy and precision. Sensitivity is reflected for example by the lower limit of quantitation (LLOQ) which is determined, according to the present invention, by taking a sample of oxyntomodulin and diluting it serially until the % CV (coefficient of variation) goes above 20%.

The term "detectably labeled" means that a polypeptide molecule of the present invention, or a complex of oxyntomodulin and polypeptide molecule, hastadedtoit, either covalently or non-covalently, a useful detectable label. In direct conjugate-labeled methods, many different useful labels can be employed including, for example, prosthetic group complexes, chromophores, chromogens (color-producing substrates), dyes, fluorescent compounds, fluorogenic compounds, radioactive isotopes, paramagnetic isotopes, and compounds that can be imaged by positron emission tomography (PET) and magnetic resonance imaging (MRI).

The nucleic acid molecules of the present invention may be expressed in a host cell after the sequences are operably linked to an expression control sequence. The expression vectors are typically replicable in the host organisms either as episomes or as an integral part of the host chromosomal DNA. Commonly, expression vectors contain selection markers, e.g., tetracycline, neomycin, and dihydrofolate reductase, to permit detection of those cells transformed with the desired polynucleotide sequences.

An expression vector containing the nucleic acid sequences of interest (e.g., the nucleic acid sequences encoding one or more of the polypeptide molecules of the invention and expression control sequences) can be transferred into a host cell by known methods, which vary depending on the type of host cells.

A polypeptide molecule of the present invention may be produced in mammalian host cells, non-limiting examples of which include CHO, NS0, HEK293 or COS cells. The host cells may be cultured using techniques known in the art. Polypeptide molecules of the present invention may be expressed and purified essentially as follows. An appropriate host cell, such as HEK 293 or CHO, may be either transiently or stably transfected with an expression system for secreting polypeptide, e.g., an antibody, using an optimal predetermined heavy chain:light chain vector ratio or a single vector system encoding both heavy chain and light chain. Nucleic acid encoding a polypeptide molecule of the present invention may be either transiently or stably transfected with an expression system for secreting polypeptide using one or more DNA molecules encoding for, e.g., an antibody heavy chain and light chain.

Various methods of protein purification may be employed to purify a polypeptide molecule of the present invention and such methods are known in the art and described, for example, in Deutscher, *Methods in Enzymology* 182: 83-89 (1990) and Scopes, *Protein Purification: Principles and Practice,* 3rd Edition, Springer, NY (1994).

For example, the medium may be conveniently applied to a MabSelect column (GE Healthcare Life Sciences), or KappaSelect column (GE Healthcare Life Sciences), that has been equilibrated with a compatible buffer, such as phosphate buffered saline (pH 7.4). The column may be washed to remove nonspecific binding components. The bound polypeptide molecule may be eluted, for example, by pH gradient (such as 20 mM Tris buffer pH 7.0 to 10 mM sodium citrate buffer pH 3.0, or phosphate buffered saline pH 7.4 to 100 mM glycine buffer pH 3.0). Antibody fractions may be detected, such as by UV absorbance or SDS-PAGE, and then may be pooled. Further purification is optional, depending on the intended use. The purified polypeptide molecules may be concentrated and/or sterile filtered using common techniques. Soluble aggregate and multimers may be effectively removed by common techniques, including size exclusion, hydrophobic interaction, ion exchange, multimodal, or hydroxyapatite chromatography. The purified polypeptide molecules may be immediately frozen at −70° C. or may be lyophilized.

The polypeptide molecules disclosed herein are useful for diagnostic, prognostic, and/or patient monitoring procedures, by detecting the level of oxyntomodulin present sum or plasma.

Useful radiolabels, which are detected simply by gamma counter, scintillation counter or autoradiography, include $^3$H, $^{124}$I, $^{125}$I, $^{131}$I, $^{35}$S, and $^{14}$C. Radionuclides can be bound to a polypeptide molecule described herein, either directly or indirectly, using a chelating agent, such as DTPA and EDTA. Examples of such radionuclides include $^{99}$Tc, $^{123}$I, $^{125}$I, $^{131}$I, $^{111}$In, $^{97}$Ru, $^{67}$Cu, $^{67}$Ga, $^{68}$Ga, $^{72}$As, $^{89}$Zr, $^{90}$Y and $^{201}$Tl.

Other suitable labels are art-known or can be determined by routine experimentation. For example, an antibody, e.g., the T-Terminal Antibody, can be conjugated with, for example, an enzyme. Binding of another antibody to human oxyntomodulin, which itself is also bound to a first the primary antibody, e.g., the C-Terminal Antibody, can then be detected by reaction with a chromogenic substrate of the enzyme under appropriate conditions to yield a detectable signal.

Colorimetric detection can be used, employing chromogenic compounds that have, or result in, chromophores with high extinction coefficients, and which are therefore easily detectable. When later exposed to its substrate under appropriate reaction conditions, the enzyme will react with the substrate to produce a chemical label that can be detected, for example, by spectrophotometric, fluorometric, or visual means.

Enzymes commonly used for this purpose include horseradish peroxidase, alkaline phosphatase, glucose-6-phosphate dehydrogenase, malate dehydrogenase, staphylococcal nuclease, delta-V-steroid isomerase, yeast alcohol dehydrogenase, alpha-glycerophosphate dehydrogenase, triose phosphate isomerase, asparaginase, glucose oxidase, β-galacto-sidase, ribonuclease, urease, catalase, glucoamylase, and acetylcholinesterase.

Non-limiting examples of suitable prosthetic group complexes include, e.g., streptavidin/biotin, avidin/biotin, and neutravidin/biotin. Use of chromogens is preferred because assays employing them can be easily performed in clinical diagnostic laboratories and reviewed by a pathologist with equipment commonly available in these laboratories. Commonly used chromogens include diaminobenzidine (DAB); DAB with enhancement; 3-amino-9-ethyl carbazole (AEC); 4-chloro-1-naphthol (4-CN); Hanker-Yates reagent; alphanaphthol pyronin; 3,3',5,5'-tetramethylbenzidine (TMB); Fast Blue BB; Fast Red TR; new fuchsin; BCIP-NBT; tetrazolium; tetranitoblue tetrazolium (TNBT); and immunogold with silver enhancement.

Useful fluorescent labels include umbelliferone, fluorescein, fluorescein isothiocyanate, dichlorotriazinylamine fluorescein, rhodamine, a dansyl group, phycoerythrin, phycocyanin, allophycocyanin, o-phthaldehyde, fluorescamine, and Cy5 (Haugland ((1996) *Handbook of Fluorescent Probes and Research Chemicals,* Sixth Ed., Molecular Probes, Eugene, OR).

Polypeptide molecules, or polypeptide molecule-oxyntomodulin complexes can also be detectably labeled using fluorescence-emitting metals, such as $^{152}$Eu$^+$, or other members of the lanthanide series, by attaching them using such metal chelating groups as diethylenetriaminepentaacetic acid (DTPA) or ethylenediamine-tetraacetic acid (EDTA).

Polypeptide molecules can also be detectably labeled by coupling them to a phosphorescent or chemiluminescent compound that can then be detected by the phosphorescence or luminescence that arises during the course of a chemical reaction. Examples of useful chemiluminescent compounds include luminol, isoluminol, theromatic acridinium ester, imidazole, acridinium salt, and oxalate ester. Likewise, a bioluminescent compound such as luciferin, luciferase, or aequorin can be used to label the antibody peptides. The presence of a bioluminescent protein is determined by detecting the presence of luminescence.

The present invention also provides articles of manufacture and kits containing compositions useful for quantifying human oxyntomodulin. The article of manufacture may comprise a container with a written label. The container may hold a composition comprising a polypeptide molecule of the present invention, which is either detectably labeled, or unlabeled.

The kit of the present invention can also comprise a container comprising a first and a second polypeptide molecule of the invention. The second polypeptide molecule can be conjugated with an enzyme or other label. A chromogenic substrate of the enzyme can also be included in the kit. The kit may further include other materials desirable from a commercial and user standpoint, including buffers, diluents, filters, needles, syringes, and package inserts with instructions for use in vivo, in vitro, or both.

The following examples are offered for illustrative purposes only, and are not intended to limit the scope of the present invention.

EXAMPLE 1

Antibody Binding Studies

Kinetic analysis and binding specificity of the N-Terminal Antibody and the C-Terminal Antibody are determined by surface plasmon resonance using Biacore T100 (GE Healthcare Life Sciences). Goat anti-mouse IgG antibody (Southern Biotech) is immobilized on a Series S CM5 sensor chip and used to capture approximately 1500 response units of anti-oxyntomodulin IgG. Binding to duplicate injections of various concentrations of human oxyntomodulin (SEQ ID NO: 25) (1.1 to 90 nmol/L) diluted in running buffer

|

(HEPES buffered saline containing 3 mmol/L EDTA and 0.05% Tween) and 22.5 nmol/L of either human glicentin span (49-89) (SEQ ID NO: 29) or human glucagon (53-81) (SEQ ID NO: 30) peptides are measured with a flow rate of 30 L/min. Kinetic constants are determined using 1:1 binding model with the T100 Evaluation software.

Using Biacore analysis of the N-Terminal Antibody, the equilibrium dissociation constant is $1.5 \times 10^{-10}$ mol/L (Table 2). The N-Terminal Antibody exhibits minimal binding to the glicentin span (48-89) peptide (SEQ ID NO: 29).

TABLE 2

Binding Kinetics of the N-terminal and C-terminal Antibodies

| Antibody | ka [(mol/L)$^{-1}*$s$^{-1}$]$^a$ | kd (s$^{-1}$) | KD (M) |
|---|---|---|---|
| N-terminal antibody | 7.2E+06 | 1.0E−03 | 1.5E−10 |
| C-terminal antibody | 1.0E+07 | 8.6E−04 | 8.3E−11 |

Using Biacore analysis of the C-Terminal Antibody, the C-Terminal Antibody dissociation constant is $8.3 \times 10^{-11}$ mol/L (Table 2). The C-Terminal Antibody exhibits minimal binding to human glucagon (53-81) (SEQ ID NO: 30).

EXAMPLE 2

Standard Curve

The optimal antibody pairing for the assay utilizes the C-Terminal Antibody as the capture antibody and N-Terminal Antibody as the detection antibody. A standard curve is prepared with synthetic human oxyntomodulin (SEQ ID NO: 25) that is serially diluted in assay buffer from a starting concentration of 50,000 ng/L. The LLOQ is determined to be 0.4 ng/L based on a 3-SD evaluation from the zero calibrator. The assay demonstrates excellent dynamic range with an upper limit of quantitation (ULOQ) of 2500 ng/L (Table 3). Since oxyntomodulin is a substrate for DDP-4 and this cleavage would remove the N-terminal neo-epitope recognized by the reporting reagent antibody, 6 sets of matched human plasma collected in either P800 or K2 EDTA collection tubes are compared to evaluate the effects from ex-vivo proteolytic degradation after sample collection. An approximate 35-40% reduction in the amount of oxyntomodulin measured with blood collected in the K2 EDTA compared to P800 tubes is observed.

Additional key attributes of the immunoassay are outlined in Table 3.

TABLE 3

Oxyntomodulin Sandwich Immunoassay Characteristics

| Parameter | Spike level | P800 EDTA plasma |
|---|---|---|
| Lower Limit of Quantitation (LLOQ) | | 0.388 ng/L |
| Upper Limit of Quantitation (ULOQ) | | 2500 ng/L |
| QC Concentrations (Low, Mid, High) | | 100, 500, and 2500 ng/L |
| QC Intra-batch Precision and | Low (CV) | 9.21% |
| Accuracy (n = 9 in one assay) | Mid (CV) | 7.03% |
| | High (CV) | 4.58% |
| QC Inter-batch Precision and | Low (CV) | 10.12% |
| Accuracy (n = 3 in one assay, | Mid (CV) | 3.54% |
| n = 24 total) | High (CV) | 3.03% |
| Dilutional Linearity | High (CV) | 12.0% |
| | Buffer (CV) | 15.0% |
| Recovery | Low (CV) | 113% |

TABLE 3-continued

Oxyntomodulin Sandwich Immunoassay Characteristics

| Parameter | Spike level | P800 EDTA plasma |
|---|---|---|
| | Mid (CV) | 102% |
| | High (CV) | 90% |
| Analyte Stability in Thawed Matrix | Low (CV) | 24.0% |
| (room temperature) (QCs stored for | Mid (CV) | 13.0% |
| 4 hours at room temperature.) | High (CV) | 17.0% |
| Analyte Stability in Thawed Matrix | Low (CV) | 14.0% |
| (4° C.) (QCs stored for 24 hours at | Mid (CV) | 0.0% |
| 4° C.) | High (CV) | 8.0% |
| Analyte Stability in Frozen Matrix | Low (CV) | 20.8% |
| (QCs stored for 12 days at −80° | Mid (CV) | 9.47% |
| C. ±10° C.) | High (CV) | 6.80% |
| Reference Range | Mean | 15.13 ng/L |
| (24 individual lots of each matrix; | Standard Dev. | 7.44 |
| n = 1) | | |

QC: Quality Controls

The intra- and inter-batch variability is ≤100/using high (2500 ng/L), mid (500 ng/L) or low (100 ng/L) oxyntomodulin concentrations. The assay demonstrates excellent dilutional linearity with <15% CV after 16-fold dilution of both assay buffer and a human plasma pool spiked with 2500 ng/L of the oxyntomodulin standard. Assay parallelism is observed with the dilution of two different human plasma samples resulting in <20% CV in the calculated values of the analyte. Robustness of the immunoassay using pooled P800 human plasma spiked with 2500, 500, 100, or 0 ng/L oxyntomodulin is demonstrated for a number of parameters. Recoveries ranged from 90-113% for all runs and ≤11% variation in calculated oxyntomodulin values is observed after six freeze-thaw cycles. Finally, the stability of the analyte in P800 collected plasma is demonstrated with <25% CV under the three different temperature conditions outlined in Table 3.

Oxyntomodulin selectivity of the immunoassay is demonstrated by testing binding to a panel of proglucagon or other biologically relevant incretin peptides. Oxyntomodulin immunoassay reactivity to three supra-physiological concentrations ranging from 2500 to 100 ng/L of human glicentin span (49-89) (SEQ ID NO: 29), human glucagon (53-81) (SEQ ID NO: 30), glucose-dependent insulinotrophic polypeptide (GIP) (SEQ ID NO: 33), GLP-1 (98-128) (SEQ ID NO: 34), GLP-1 (100-128) (SEQ ID NO: 35), oxyntomodulin (55-89) (SEQ ID NO: 26), oxyntomodulin (56-89) (SEQ ID NO: 27) is measured. The glicentin span (49-89) (SEQ ID NO: 29) and GIP (SEQ ID NO: 33), peptides are the only analytes that are measured above background levels at the highest concentration. The 500 ng/L concentration of glicentin span (49-89) (SEQ ID NO: 29) also provide a signal slightly above those seen for the buffer blank controls. For comparison and in stark contrast to the glicentin span results, >170,000, >30,000 and >8,000 ECL units are observed with 2500, 500 and 100 ng/L of human oxyntomodulin (53-89) (SEQ ID NO: 25), respectively.

The cross-reactivity of the oxyntomodulin immunoassay is minimal; <0.5% for the glicentin span (49-89) peptide (SEQ ID NO: 29) (which is a surrogate for glicentin cross-reactivity) and 0.12% for GIP peptide (SEQ ID NO: 33). No signal is observed with oxyntomodulin (55-89) peptide (SEQ ID NO: 26) or oxyntomodulin (56-89) peptide (SEQ ID NO: 27), which are N-terminal truncations of human oxyntomodulin of 2 or 3 residues, respectively. No signal is observed when sampling human plasma in which isotype-matched irrelevant antibodies are substituted for either the capture or detection reagent.

EXAMPLE 3

Sandwich Assay

Meso Scale Discovery (MSD) Streptavidin Gold Multi-array 96-well plates (Meso Scale Diagnostics) are washed three times with 1× Tris buffered saline (TBS) containing 10 mmol/L Tris pH 7.4, 150 mmol/L NaCl with 1 mL Tween 20/L and blocked with 200 μL of TBS containing 1% (w/v) BSA (Sigma). After one hour, 50 μL of biotin-labeled C-terminal Antibody at a concentration of 1 mg/L is allowed to bind to the plate for an additional hour at room temperature (RT). Oxyntomodulin peptide standards diluted with assay buffer consisting of 50 mmol/L HEPES, pH7.4, 150 mmol/L NaCl, 10 mL/L Triton X-100, 5 mmol/L each EDTA and EGTA, 1% (w/v) BSA, both protease (Roche) and dipeptidyl peptidase-4 (DPP-4) (Millipore) inhibitors, and 100 mg/L Heterophilic Blocking Reagent 1 (Scantibodies) are added to the wells to generate a standard calibration curve. In the same assay buffer, plasma samples are diluted 1:2 and both samples and standards are incubated overnight at 4° C. The plate is washed and 50 μL of 1 ng/mL ruthenium-labeled N-Terminal Antibody is added to the wells and allowed to incubate for 1 hour at RT. Following a final wash step, 150 μL of 2×MSD read buffer is added and a MSD SECTOR Imager 600 (Meso Scale Diagnostics) reader is used to measure ruthenium electrochemilumines-cence units (ECL).

Human Plasma Samples. Blood samples from healthy men and women, from 18-65 years of age, are collected into P800 EDTA BD™ Vacutainer (BD Biosciences) collection tubes with informed consent. Samples are stored on ice and spun-down at 4° C. with a bench-top centrifuge at 2000 g for 20 minutes within one hour of collection. Resultant plasma samples are stored at −70° C. prior to analysis of oxynto-modulin levels. K2 and P800 EDTA plasma are also obtained from an additional 19 healthy volunteers under conditions of 10 hour fasting, 5-10 and 90-120 minutes postprandial. The postprandial collection follows a mixed meal challenge consisting of approximately 262 fat calories, 274 carbohydrate calories, and 100 protein calories.

Oxyntomodulin Levels in Normal Human Plasma. The sandwich immunoassay is used to determine the effect of a nutritional challenge on oxyntomodulin plasma levels in healthy individuals. Blood is collected in both P800 and K2 EDTA tubes from 19 volunteers after an overnight fast. Samples are also collected both within a few minutes and within 2 hours after consumption of a standardized mixed meal. Oxyntomodulin values from samples collected with K2 EDTA tubes are lower compared to those collected with P800 collection tubes for all three time points analyzed. The levels of oxyntomodulin increases immediately following feeding. The baseline, early and later time point means for the P800 samples are 11±9 ng/L, 21±9 ng/L and 33±14 ng/L, respectively. Baseline, early and later time point means for the K2 EDTA samples are 87 ng/L, 14±6 ng/L and 23±11 ng/L, respectively.

All data are expressed as means f SEM. MSD Workbench software is used for each of the 4 PL fit calibration curves and interpolation of unknown values. Data are plotted with SigmaPlot version 11.0, and Microsoft Office Excel 2010 or GraphPad Prism 6 is used for data analysis. In each case a p-value of ≤0.05 is considered to indicate statistical significance. Percent cross-reactivities are determined as the ratio of the ECL counts with the peptide of interest to the ECL counts with the reference human oxyntomodulin (53-89) (SEQ ID NO: 25) peptide after subtraction of the buffer blank ECL counts for each concentration tested.

Oxyntomodulin antibody affinities are increased 6 to >200-fold. Intra- and inter-assay CVs are 7-10% and 3-10%, respectively. Spike recovery ranges from 90-113%, linearity is evident up to a 16-fold dilution and glicentin cross-reactivity is 0.5%. Oxyntomodulin levels are lower in K2 EDTA relative to P800 plasma. Postprandial increases in oxyntomodulin occur within minutes and the levels signifi-cantly correlated with those obtained using IA-LC-MS.

The oxyntomodulin sandwich immunoassay is appropri-ately sensitive, selective and is also amendable to high throughput application for the reliable determination of endogenous levels of intact oxyntomodulin from human samples.

The combination of a pair of antibodies that bind to specific human oxyntomodulin N- and C-terminal epitopes, which are present only on the respective proglucagon frag-ments, facilitates the creation of an immunoassay with sufficient selectivity and sensitivity to determine endog-enous levels of human oxyntomodulin.

Selectivity of the immunoassay is initially assessed with other proglucagon derived and incretin peptides of interest. A small signal is observed with the highest spike of glicentin span (49-89) peptide (SEQ ID NO: 29) in the oxyntomodu-lin sandwich immunoassay; however, this signal is more than 2 orders of magnitude lower than that obtained with the same concentration of human oxyntomodulin (SEQ ID NO: 25). Endogenous glicentin has been reported to increase in a postprandial fashion and peak at 130 pmol/L (Naito H, et al., *Regul. Pept.* 1999; 79:55-61), and that level is still lower than the high spike concentration (2500 ng/L [560 pmol/L]) used in the studies herein, indicating that endogenous gli-centin levels do not impact the human oxyntomodulin sandwich immunoassay herein.

Human oxyntomodulin has a short half-life (minutes) in circulation (Schjoldager B T, et al., *Eur. J. Clin. Invest.* 1988; 18:499-5), and has been shown to be a substrate for prote-olysis by DPP-4 (Yi J, et al., *PLoS One* 2015; 10:e0134427; Zhu L, et al., *J. Biol. Chem.* 2003; 278: 22418-23), which removes the first 2 amino-terminal residues. Selectivity of the novel N-terminal neo-epitope antibody disclosed herein (SEQ ID NOS: 9 and 10) is confirmed by the complete lack of reactivity to synthetic oxyntomodulin peptides missing the first 2 or 3 residues (SEQ ID NOS: 26 and 27, respec-tively). A small but reproducible reduction in the amount of human oxyntomodulin (SEQ ID NO: 25) measured using the sandwich immunoassay herein is observed in sera collected with K2 EDTA, relative to P800 tubes, which confirms that endogenous human oxyntomodulin is processed by DDP-4 or some other related protease that removes N-terminal amino acids, and the sandwich immunoassay disclosed herein selectively measures only the intact human oxynto-modulin (SEQ ID NO: 25) component.

Human K2 EDTA and P800 plasma (500 μL) is spiked with human oxyntomodulin (53-89) SEQ ID NO: 25, oxyn-tomodulin (55-89) SEQ ID NO: 26 and oxyntomodulin (56-89) SEQ ID: 27 stable-isotope labeled internal standard peptides (CPC Scientific) and diluted with I buffer (25 mmol/L Tris-HCl, 25 mmol/L HEPES, 300 mmol/L NaCl, 0.1% (v/v) octyl β-D-glucopyranoside, pH 7.5). Immunoaf-finity enrichment is allowed to proceed overnight at 4° C. following the addition of 2 μg of a biotinylated anti-gluca-gon antibody (Sloan J H, et al., *Clin. Biochem.* 2012;

45:1640-4). After incubation, 50 μL of Dynabeads™ MyOne™ streptavidin T1 magnetic beads (ThermoFisher Scientific) are added to the mixture followed by incubation for 30 minutes at RT. The beads are then sequentially washed once with 1 mL of each of the following 3 buffers: radio-immunoprecipitation assay buffer (ThermoFisher Scientific), a buffer consisting of 25 mmol/L Tris-HCl, 25 mmol/L HEPES, 500 mmol/L NaCl, 0.1% (v/v) octyl β-D-glucopyranoside pH 7.5, and deionized water. Bound analytes ae eluted with 50 μL of 0.2% (v/v) formic acid/1× Invitrosol™ (ThermoFisher Scientific)/10% (v/v) acetonitrile. Protein quantification is achieved via high resolution accurate mass LC-MS using a Thermo Scientific Q Exactive mass spectrometer.

Fasting oxyntomodulin levels in healthy human volunteers are found to range from 7-11 ng/L, depending on the collection method employed, and rise within 10 minutes of feeding to levels ranging from 23-33 ng/L at the latest time point collected. These results are consistent with those obtained using the IA-LC-MS assay discussed below, as well as by the LC-MS assay of Lee et al. (Lee A Y, et al., *Clin. Chem.* 2015; 62: 227-235).

EXAMPLE 4

Correlation of Sandwich Assay Results with Immunoassay-LC-MS Assay Results

An oxyntomodulin analytical reference standard is not currently available to gauge the accuracy of the immunoassay. However, immunoassay-LC-MS has the distinct advantage of identifying the molecular forms of an analyte of interest present in a given sample (Bouillon R, et al., *Clin. Chem.* 2016; 62: 6-8).

The correlation of oxyntomodulin levels obtained with the sandwich immunoassay is examined with those obtained using the immunoassay-LC-MS method of Cox et al. (Cox J M, et al., *Bioanalysis* 2016; 8:1579-95) on the same set of plasma samples employed in the sandwich assay above. The correlation between the sandwich assay and the immunoassay-LC-MS method is high (Spearman coefficient 0.9236; P<0.0001), and confirms the selectivity of the sandwich immunoassay of the invention.

Moreover, the sandwich immunoassay of the invention enables scalability and high-throughput application, reduction in sample volumes and assay time, and obviates the need for extensive investment in equipment and expertise, relative to the use of immunoassay-LC-MS assays. Use of the sensitive and selective sandwich immunoassay disclosed herein to measure human oxyntomodulin in human samples can also facilitate an improved understanding of oxyntomodulin biology.

Sequences

SEQ ID NO: 1
GYTFTDYAFS

SEQ ID NO: 2
WITTNTGEATYADDFKG

SEQ ID NO: 3
ETEYGDSSWFGH

SEQ ID NO: 4
RASESVDGWGNSFMH

SEQ ID NO: 5
LATYRVA

-continued

SEQ ID NO: 6
MQSSEDPYT

SEQ ID NO: 7
QIQLVQSGPELKKPGETVKISCKASGYTFTDYAFSWVKQA

PGKGLKWMGWITTNTGEATYADDFKGRFAFSLETSASTAY

LQISNLKNEDTATYFCARETEYGDSSWFGHWGQGTLVTVS

A

SEQ ID NO: 8
DIVLTQSPASLAVSLGQRATISCRASESVDGWGNSFMHWY

QQKPGQPPKLLIYLATYRVAGIPARFSGSGSRTDFTLTIN

PVEADDVATYYCMQSSEDPYTFGGGTKLEIK

SEQ ID NO: 9
QIQLVQSGPELKKPGETVKISCKASGYTFTDYAFSWVKQA

PGKGLKWMGWITTNTGEATYADDFKGRFAFSLETSASTAY

LQISNLKNEDTATYFCARETEYGDSSWFGHWGQGTLVTVS

AAKTTAPSVYPLAPVCGDTTGSSVTLGCLVKGYFPEPVTL

TWNSGSLSSGVHTFPAVLQSDLYTLSSSVTVTSSTWPSQS

ITCNVAHPASSTKVDKKIEPRGPTIKPCPPCKCPAPNLLG

GPSVFIFPPKIKDVLMISLSPIVTCVVVDVSEDDPDVQIS

WFVNNVEVHTAQTQTHREDYNSTLRVVSALPIQHQDWMSG

KEFKCKVNNKDLPAPIERTISKPKGSVRAPQVYVLPPPEE

EMTKKQVTLTCMVTDFMPEDIYVEWTNNGKTELNYKNTEP

VLDSDGSYFMYSKLR VEKKNWVERNSYSCSVVHEGLHNH

HTTKSFSRTPGK

SEQ ID NO: 10
DIVLTQSPASLAVSLGQRATISCRASESVDGWGNSFMHWY

QQKPGQPPKLLIYLATYRVAGIPARFSGSGSRTDFTLTIN

PVEADDVATYYCMQSSEDPYTFGGGTKLEIKRADAAPTVS

IFPPSSEQLTSGGASVVCFLNNFYPKDINVKWKIDGSERQ

NGVLNSWTDQDSKDSTYSMSSTLTLTKDEYERHNSYTCEA

THKTSTSPIVKSFNRNEC

SEQ ID NO: 11
cagatccagttggtacagtctggacctgagctgaagaagc ctggagagacagtcaagatctcctgcaaggcttctgggta taccttcacagactatgcatttagctgggtgaaacaggct ccaggaaagggtttaaagtggatgggctggataaccacta acactggagaagccacatatgctgatgacttcaagggacg gtttgccttctctttggaaacctctgccagcactgcctat ttgcagatcagcaacctcaaaaatgaggacacggctacat atttctgtgcaagagagacggaatacggtgatagctcctg gtttgggcactggggccaagggactctggtcactgtctct gcagctaaaacaacagccccatcggtctatccgctagccc ctgtgtgtggagatacaactggctcctcggtgactctagg -continued

```
atgcctggtcaaggggttatttccctgagccagtgaccttg acctggaactctggcagcctgtccagtggtgtgcacacct tcccagctgtcctgcagtctgacctctacaccctcagcag ctcagtgactgtaacgtcgagcacctggcccagccagtcc atcacctgcaatgtggcccacccggcaagcagcaccaagg tggacaagaaaattgagcccagagggcccacaatcaagcc ctgtcctccatgcaaatgcccagcacctaacctcttgggg gaccatccgtcttcatcttccctccaaagatcaaggatgt actcatgatctccctgagccccatagtcacatgtgtggtg gtggatgtgagcgaggatgacccagatgtccagatcagct ggtttgtgaacaacgtggaagtacacacagctcagacaca aacccatagagaggattacaacagtactctccgggtggtc agtgccctcccatccagcaccaggactggatgagtggca aggagttcaaatgcaaggtcaacaacaaagacctcccagc gcccatcgagagaaccatctcaaaacccaaagggtcagta agagctccacaggtatatgtcttgcctccaccagaagaag agatgactaagaaacaggtcactctgacctgcatggtcac agacttcatgcctgaagacatttacgtggagtggaccaac aacgggaaaacagagctaaactacaagaacactgaaccag tcctggactctgatggttcttacttcatgtacagcaagct gagagtggaaaagaagaactgggtggaaagaaatagctac tcctgttcagtggtccacgagggtctgcacaatcaccaca cgactaagagcttctcccggactccgggtaaa
```

SEQ ID NO: 12
```
gacattgtgctgacccaatctccagcttctttggccgtgt ctctagggcagagggccaccatatcctgcagagccagtga aagtgttgatggatggggcaatagtttcatgcactggtac cagcagaaaccaggacagccacccaaactcctcatctatc tcgctacctatcgcgtagctgggatccctgccaggttcag tggcagtgggtctaggacagacttcaccctcaccattaat cctgtggaggctgatgatgttgcaacctattattgtatgc agagtagtgaagatccgtacacgttcggagggggaccaa gctggaaataaaacgggctgatgcggcgcccactgtatcc atcttcccaccatccagtgagcagttaacatctggaggtg ctagcgtcgtgtgcttcttgaacaacttctaccccaaaga catcaatgtcaagtggaagattgatggcagtgaacgacaa aatggcgtcctgaacagttggactgatcaggacagcaaag acagcacctacagcatgagcagcaccctcacgttgaccaa ggacgagtatgaacgacataacagctataccctgtgaggcc actcacaagacatcaacttcacccattgtcaagagcttca acaggaatgagtgt
```

-continued

SEQ ID NO: 13
```
GYNFTNYWLH
```

SEQ ID NO: 14
```
ELDPEYGFANYNQKFKG
```

SEQ ID NO: 15
```
GFMDY
```

SEQ ID NO: 16
```
RSSRSLLDPDGKTYLN
```

SEQ ID NO: 17
```
LVSKLDS
```

SEQ ID NO: 18
```
WQGTHLPVT
```

SEQ ID NO: 19
```
QVQVQQSGAELVMPGTSVKLSCKASGYNFTNYWLHWVKQR

PGQGLEWIGELDPEYGFANYNQKFKGKATLTVDKSSSTAY

MQLSSLTSEDSAVYYCSAGFMDYWGQGTSVTVSS
```

SEQ ID NO: 20
```
DVVMTQTPLTLSVNIGQPASISCRSSRSLLDPDGKTYLNW

LLQRPGQSPKRLIYLVSKLDSRVPDRFTGSGSGTDFTLKI

SRVEAEDLGVYYCWQGTHLPVTFGGGTKLEIK
```

SEQ ID NO: 21
```
QVQVQQSGAELVMPGTSVKLSCKASGYNFTNYWLHWVKQR

PGQGLEWIGELDPEYGFANYNQKFKGKATLTVDKSSSTAY

MQLSSLTSEDSAVYYCSAGFMDYWGQGTSVTVSSAKTTAP

SVYPLAPVCGDTTGSSVTLGCLVKGYFPEPVTLTWNSGSL

SSGVHTFPAVLQSDLYTLSSSVTVTSSTWPSQSITCNVAH

PASSTKVDKKIEPRGPTIKPCPPCKCPAPNLLGGPSVFIF

PPKIKDVLMISLSPIVTCVVVDVSEDDPDVQISWFVNNVE

VHTAQTQTHREDYNSTLRVVSALPIQHQDWMSGKEFKCKV

NNKDLPAPIERTISKPKGSVRAPQVYVLPPPEEEMTKKQV

TLTCMVTDFMPEDIYVEWTNNGKTELNYKNTEPVLDSDGS

YFMYSKLRVEKKNWVERNSYSCSVVHEGLHNHHTTKSFSR

TPGK
```

SEQ ID NO: 22
```
DVVMTQTPLTLSVNIGQPASISCRSSRSLLDPDGKTYLNW

LLQRPGQSPKRLIYLVSKLDSRVPDRFTGSGSGTDFTLKI

SRVEAEDLGVYYCWQGTHLPVTFGGGTKLEIKRADAAPTV

SIFPPSSEQLTSGGASVVCFLNNFYPKDINVKWKIDGSER

QNGVLNSWTDQDSKDSTYSMSSTLTLTKDEYERHNSYTCE

ATHKTSTSPIVKSFNRNEC
```

SEQ ID NO: 23
```
caggtccaagtgcagcagtctggggctgagcttgtgatgc ctgggacttcagtgaagctgtcctgcaaggcctctggcta taacttcactaattattggttacactgggtgaagcagagg cctggacaaggccttgagtggatcggagagctcgaccctg aatatggttttgcgaactacaatcaaaagttcaagggcaa
```

-continued

```
ggccacattgactgtagacaaatcctccagcacagcctac atgcagctcagcagcctgacatctgaggactctgcggtct attactgttctgccgggttcatggactactggggtcaagg aacctcagtcaccgtctcctcagctaaaacaacagcccca tcggtctatccgctagccctgtgtgtggagatacaactg gctcctcggtgactctaggatgcctggtcaagggttattt ccctgagccagtgaccttgacctggaactctggcagcctg tccagtggtgtgcacaccttcccagctgtcctgcagtctg acctctacaccctcagcagctcagtgactgtaacgtcgag cacctggcccagccagtccatcacctgcaatgtggcccac ccggcaagcagcaccaaggtggacaagaaaattgagccca gagggcccacaatcaagccctgtcctccatgcaaatgccc agcacctaacctcttgggtggaccatccgtcttcatcttc cctccaaagatcaaggatgtactcatgatctccctgagcc ccatagtcacatgtgtggtggtggatgtgagcgaggatga cccagatgtccagatcagctggtttgtgaacaacgtggaa gtacacacagctcagacacaaacccatagagaggattaca acagtactctccgggtggtcagtgccctccccatccagca ccaggactggatgagtggcaaggagttcaaatgcaaggtc aacaacaaagacctcccagcgcccatcgagagaaccatct caaaacccaaagggtcagtaagagctccacaggtatatgt cttgcctccaccagaagaagagatgactaagaaacaggtc actctgacctgcatggtcacagacttcatgcctgaagaca tttacgtggagtggaccaacaacgggaaaacagagctaaa ctacaagaacactgaaccagtcctggactctgatggttct tacttcatgtacagcaagctgagagtggaaaagaagaact gggtggaaagaaatagctactcctgttcagtggtccacga gggtctgcacaatcaccacacgactaagagcttctcccgg actccgggtaaa
```

SEQ ID NO: 24
```
gatgttgtgatgacccagactccactcactttgtcggtta acattggacaaccagcctccatctcttgcaggtcaagtcg gagcctcttagatccagatggaaagacatatttgaattgg ttgttacagaggccaggccagtctccaaagcgcctaatct atctggtgtctaaactggactctagagtccctgacaggtt
```

-continued

```
cactggcagtggatcagggacagatttcacactgaaaatc agcagagtggaggctgaggatttgggagtttattattgct ggcaaggtacacatcttcctgtaacgttcggtggaggcac caagctggaaatcaaacgggctgatgcggcgcccactgta tccatcttcccaccatccagtgagcagttaacatctggag gtgctagcgtcgtgtgcttcttgaacaacttctaccccaa agacatcaatgtcaagtggaagattgatggcagtgaacga caaaatggcgtcctgaacagttggactgatcaggacagca aagacagcacctacagcatgagcagcaccctcacgttgac caaggacgagtatgaacgacataacagctatacctgtgag gccactcacaagacatcaacttcacccattgtcaagagct tcaacaggaatgagtgt
```

SEQ ID NO: 25
HSQGTFTSDYSKYLDSRRAQDFVQWLMNTKRNRNNIA

SEQ ID NO: 26
QGTFTSDYSKYLDSRRAQDFVQWLMNTKRNRNNIA

SEQ ID NO: 27
GTFTSDYSKYLDSRRAQDFVQWLMNTKRNRNNIA

SEQ ID NO: 28
RSLQDTEEKSRSFSASQADPLSDPDQMNEDKRHSQGTFTS

DYSKYLDSRRAQDFVQWLMNTKRNRNNIA

SEQ ID NO: 29
EDKRHSQGTFTSDYSKYLDSRRAQDFVQWLMNTKRNRNNIA

SEQ ID NO: 30
HSQGTFTSDYSKYLDSRRAQDFVQWLMNT

SEQ ID NO: 31
QGTFTSDYSKYLDSRRAQDFVQWLMNT

SEQ ID NO: 32
GTFTSDYSKYLDSRRAQDFVQWLMNT

SEQ ID NO: 33
YAEGTFISDYSIAMDKIHQQDFVNWLLAQKGKKNDWKHNITQ

SEQ ID NO: 34
HAEGTFTSDVSSYLEGQAAKEFIAWLVKGRG

SEQ ID NO: 35
EGTFTSDVSSYLEGQAAKEFIAWLVKGRG

SEQ ID NO: 36
MKSIYFVAGLFVMLVQGSWQRSLQDTEEKSRSFSASQADP

LSDPDQMNEDKRHSQGTFTSDYSKYLDSRRAQDFVQWLMN

TKRNRNNIAKRHDEFERHAEGTFTSDVSSYLEGQAAKEFI

AWLVKGRGRRDFPEEVAIVEELGRRHADGSFSDEMNTILD

NLAARDFINWLIQTKITDRK

---

We claim:

1. A polypeptide molecule selected from the group consisting of
   (a) a polypeptide molecule that binds the N-terminal region of each of human oxyntomodulin (SEQ ID NO: 25) and human glucagon (SEQ ID NO: 30), wherein the polypeptide molecule comprises the complementarity determining regions (CDRs) set forth in SEQ ID NOS: 1-6 and
   (b) a polypeptide molecule that binds the C-terminal region in each of human oxyntomodulin (SEQ ID NO: 25) and human glicentin (SEQ ID NO: 28), wherein the polypeptide molecule comprises the complementarity determining regions (CDRs) set forth in SEQ ID NOS: 13-18.

2. The polypeptide molecule of claim 1, wherein the polypeptide molecule is an antibody.

3. The polypeptide molecule of claim 1, wherein the polypeptide molecule is an scFv or a Fab.

4. The polypeptide molecule of claim 1(a), wherein the polypeptide molecule is an antibody comprising a heavy chain variable region (VH) comprising SEQ ID NO: 7 and a light chain variable region (VL) comprising SEQ ID NO: 8.

5. The polypeptide molecule of claim 4, wherein the polypeptide molecule is an antibody comprising a heavy chain comprising SEQ ID NO: 9 and a light chain comprising SEQ ID NO: 10.

6. The polypeptide molecule of claim 5, wherein the polypeptide molecule is an antibody comprising a heavy chain consisting of SEQ ID NO: 9 and a light chain consisting of SEQ ID NO: 10.

7. A nucleic acid molecule selected from the group consisting of
   (a) a nucleic acid molecule comprising one or both of a first nucleic acid sequence encoding SEQ ID NO: 9 and a second nucleic acid sequence encoding SEQ ID NO: 10 and
   (b) a nucleic acid molecule comprising one or both of a first nucleic acid sequence encoding SEQ ID NO: 21 and a second nucleic acid sequence encoding SEQ ID NO: 22.

8. The nucleic acid molecule of claim 7(a), wherein the first nucleic acid sequence encoding SEQ ID NO: 9 comprises SEQ ID NO: 11, and wherein the second nucleic acid sequence encoding SEQ ID NO: 10 comprises SEQ ID NO: 12.

9. A vector selected from the group consisting of
   (a) a vector comprising one or both of a first nucleic acid sequence encoding SEQ ID NO: 9 and a second nucleic acid sequence encoding SEQ ID NO: 10 and
   (b) a vector comprising one or both of a first nucleic acid sequence encoding SEQ ID NO: 21 and a second nucleic acid sequence encoding SEQ ID NO: 22.

10. A composition comprising the vector of claim 9.

11. A cell comprising the vector of claim 9.

12. The cell of claim 11, wherein the cell is a mammalian cell.

13. A process of producing a polypeptide molecule, comprising culturing a cell comprising
   (a) one or both of a first nucleic acid sequence encoding SEQ ID NO: 9 and a second nucleic acid sequence encoding SEQ ID NO: 10 or
   (b) one or both of a first nucleic acid sequence encoding SEQ ID NO: 21 and a second nucleic acid sequence encoding SEQ ID NO: 22,
   under conditions such that the polypeptide molecule is expressed, and recovering the expressed polypeptide molecule from the culture medium.

14. A polypeptide molecule produced by the process of claim 13.

15. A composition comprising the polypeptide molecule of claim 14.

16. The polypeptide molecule of claim 1(b), wherein the polypeptide molecule is an antibody comprising a VH comprising SEQ ID NO: 19 and a VL comprising SEQ ID NO: 20.

17. The polypeptide molecule of claim 16, wherein the polypeptide molecule is an antibody comprising a heavy chain comprising SEQ ID NO: 21 and a light chain comprising SEQ ID NO: 22.

18. The polypeptide molecule of claim 17, wherein the polypeptide molecule is an antibody comprising a heavy chain consisting of a SEQ ID NO: 21 and a light chain consisting of SEQ ID NO: 22.

19. The nucleic acid molecule of claim 7(b), wherein the first nucleic acid sequence encoding SEQ ID NO: 21 comprises SEQ ID NO: 23, and wherein the second nucleic acid sequence encoding SEQ ID NO: 22 comprises SEQ ID NO: 24.

20. A composition comprising the polypeptide of claim 1.

21. A method of determining the concentration of human oxyntomodulin (SEQ ID NO: 25) in a liquid sample, comprising:

(a) contacting a liquid sample comprising human oxyntomodulin with a first polypeptide molecule that binds the C-terminal region in each of human oxyntomodulin (SEQ ID NO: 25) and human glicentin (SEQ ID NO: 28), wherein the first polypeptide molecule comprises the CDRs of SEQ ID NOS: 13-18, thereby forming a first polypeptide molecule-human oxyntomodulin complex;

(b) contacting the first polypeptide molecule-human oxyntomodulin complex with a second polypeptide molecule that binds the N-terminal region of each of human oxyntomodulin (SEQ ID NO: 25) and human glucagon (SEQ ID NO: 30), wherein the second polypeptide molecule comprises the CDRs of SEQ ID NOS: 1-6, thereby forming a first polypeptide molecule-human oxyntomodulin-second polypeptide molecule complex; and (c) quantitating the amount of oxyntomodulin in the first polypeptide molecule-human oxyntomodulin-second polypeptide molecule complex by comparison against a standard curve of known amounts of human oxyntomodulin (SEQ ID NO: 25).

22. The method of claim 21, wherein the liquid sample is serum or plasma.

23. The method of claim 21, wherein the first polypeptide molecule is an antibody and the second polypeptide molecule is an antibody.

24. The method of claim 21, wherein the first polypeptide molecule is an antibody comprising a VH comprising SEQ ID NO: 19 and a VL comprising SEQ ID NO: 20, and the second polypeptide molecule is an antibody comprising a VH comprising SEQ ID NO: 7 and a VL comprising SEQ ID NO: 8.

25. The method of claim 21, wherein the first polypeptide molecule is an antibody comprising a heavy chain comprising SEQ ID NO: 21 and comprising a light chain comprising SEQ ID NO: 22, and the second polypeptide molecule is an antibody comprising a heavy chain comprising SEQ ID NO: 9 and a light chain comprising SEQ ID NO: 10.

26. The method of claim 21, wherein the first polypeptide molecule is an antibody comprising a heavy chain consisting of SEQ ID NO: 21 and a light chain consisting of SEQ ID NO: 22, and the second polypeptide molecule is an antibody comprising a heavy chain consisting of SEQ ID NO: 9 and a light chain consisting of SEQ ID NO: 10.

* * * * *

SEQUENCE LISTING

<160> NUMBER OF SEQ ID NOS: 36

<210> SEQ ID NO 1
<211> LENGTH: 10
<212> TYPE: PRT

<210> ORGANISM: Artificial Sequence
<220> FEATURE:
<223> OTHER INFORMATION: Synthetic Construct

<400> SEQUENCE: 1

Gly Tyr Thr Phe Thr Asp Tyr Ala Phe Ser
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Trp Ile Thr Thr Asn Thr Gly Glu Ala Thr Tyr Ala Asp Asp Phe Lys
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: Synthetic Construct

<400> SEQUENCE: 3

Glu Thr Glu Tyr Gly Asp Ser Ser Trp Phe Gly His
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Synthetic Construct

<400> SEQUENCE: 4

Arg Ala Ser Glu Ser Val Asp Gly Trp Gly Asn Ser Phe Met His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Leu Ala Thr Tyr Arg Val Ala
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Met Gln Ser Ser Glu Asp Pro Tyr Thr
1               5

<210> SEQ ID NO 7
<211> LENGTH: 121

<212> TYPE: PRT
<213> ORGANISM: Artificial Sequence
<220> FEATURE:
<223> OTHER INFORMATION: Synthetic Construct

<400> SEQUENCE: 7

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ala Phe Ser Trp Val Lys Gln Ala Pro Gly Lys Gly Leu Lys Trp Met
            35                  40                  45

Gly Trp Ile Thr Thr Asn Thr Gly Glu Ala Thr Tyr Ala Asp Asp Phe
        50                  55                  60

Lys Gly Arg Phe Ala Phe Ser Leu Glu Thr Ser Ala Ser Thr Ala Tyr
65                  70                  75                  80

Leu Gln Ile Ser Asn Leu Lys Asn Glu Asp Thr Ala Thr Tyr Phe Cys
                85                  90                  95

Ala Arg Glu Thr Glu Tyr Gly Asp Ser Ser Trp Phe Gly His Trp Gly
            100                 105                 110

Gln Gly Thr Leu Val Thr Val Ser Ala
        115                 120
```

<210> SEQ ID NO 8
<211> LENGTH: 111
<212> TYPE: PRT
<213> ORGANISM: Artificial Sequence
<220> FEATURE:
<223> OTHER INFORMATION: Synthetic Construct

<400> SEQUENCE: 8

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Gly Trp
            20                  25                  30

Gly Asn Ser Phe Met His Trp Tyr Gln Gln Lys Pro Gly Gln Pro Pro
        35                  40                  45

Lys Leu Leu Ile Tyr Leu Ala Thr Tyr Arg Val Ala Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Met Gln Ser Ser
                85                  90                  95

Glu Asp Pro Tyr Thr Phe Gly Gly Gly Thr Lys Leu Glu Ile Lys
            100                 105                 110
```

<210> SEQ ID NO 9
<211> LENGTH: 451
<212> TYPE: PRT
<213> ORGANISM: Artificial Sequence
<220> FEATURE:
<223> OTHER INFORMATION: Synthetic Construct

<400> SEQUENCE: 9

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ala Phe Ser Trp Val Lys Gln Ala Pro Gly Lys Gly Leu Lys Trp Met
```

```
          35              40              45
Gly Trp Ile Thr Thr Asn Thr Gly Glu Ala Thr Tyr Ala Asp Asp Phe
    50              55              60

Lys Gly Arg Phe Ala Phe Ser Leu Glu Thr Ser Ala Ser Thr Ala Tyr
65              70              75              80

Leu Gln Ile Ser Asn Leu Lys Asn Glu Asp Thr Ala Thr Tyr Phe Cys
                85              90              95

Ala Arg Glu Thr Glu Tyr Gly Asp Ser Ser Trp Phe Gly His Trp Gly
            100             105             110

Gln Gly Thr Leu Val Thr Val Ser Ala Ala Lys Thr Thr Ala Pro Ser
            115             120             125

Val Tyr Pro Leu Ala Pro Val Cys Gly Asp Thr Thr Gly Ser Ser Val
    130             135             140

Thr Leu Gly Cys Leu Val Lys Gly Tyr Phe Pro Glu Pro Val Thr Leu
145             150             155             160

Thr Trp Asn Ser Gly Ser Leu Ser Ser Gly Val His Thr Phe Pro Ala
            165             170             175

Val Leu Gln Ser Asp Leu Tyr Thr Leu Ser Ser Ser Val Thr Val Thr
            180             185             190

Ser Ser Thr Trp Pro Ser Gln Ser Ile Thr Cys Asn Val Ala His Pro
            195             200             205

Ala Ser Ser Thr Lys Val Asp Lys Lys Ile Glu Pro Arg Gly Pro Thr
    210             215             220

Ile Lys Pro Cys Pro Pro Cys Lys Cys Pro Ala Pro Asn Leu Leu Gly
225             230             235             240

Gly Pro Ser Val Phe Ile Phe Pro Pro Lys Ile Lys Asp Val Leu Met
            245             250             255

Ile Ser Leu Ser Pro Ile Val Thr Cys Val Val Val Asp Val Ser Glu
            260             265             270

Asp Asp Pro Asp Val Gln Ile Ser Trp Phe Val Asn Asn Val Glu Val
    275             280             285

His Thr Ala Gln Thr Gln Thr His Arg Glu Asp Tyr Asn Ser Thr Leu
    290             295             300

Arg Val Val Ser Ala Leu Pro Ile Gln His Gln Asp Trp Met Ser Gly
305             310             315             320

Lys Glu Phe Lys Cys Lys Val Asn Asn Lys Asp Leu Pro Ala Pro Ile
            325             330             335

Glu Arg Thr Ile Ser Lys Pro Lys Gly Ser Val Arg Ala Pro Gln Val
            340             345             350

Tyr Val Leu Pro Pro Pro Glu Glu Glu Met Thr Lys Lys Gln Val Thr
            355             360             365

Leu Thr Cys Met Val Thr Asp Phe Met Pro Glu Asp Ile Tyr Val Glu
    370             375             380

Trp Thr Asn Asn Gly Lys Thr Glu Leu Asn Tyr Lys Asn Thr Glu Pro
385             390             395             400

Val Leu Asp Ser Asp Gly Ser Tyr Phe Met Tyr Ser Lys Leu Arg Val
            405             410             415

Glu Lys Lys Asn Trp Val Glu Arg Asn Ser Tyr Ser Cys Ser Val Val
            420             425             430

His Glu Gly Leu His Asn His His Thr Thr Lys Ser Phe Ser Arg Thr
            435             440             445

Pro Gly Lys
    450
```

```
<210> SEQ ID NO 10
<211> LENGTH: 218
<212> TYPE: PRT
<213> ORGANISM: Artificial Sequence
<220> FEATURE:
<223> OTHER INFORMATION: Synthetic Construct

<400> SEQUENCE: 10

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Gly Trp
            20                  25                  30

Gly Asn Ser Phe Met His Trp Tyr Gln Gln Lys Pro Gly Gln Pro Pro
        35                  40                  45

Lys Leu Leu Ile Tyr Leu Ala Thr Tyr Arg Val Ala Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Met Gln Ser Ser
            85                  90                  95

Glu Asp Pro Tyr Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 11
<211> LENGTH: 1353
<212> TYPE: DNA
<213> ORGANISM: Artificial Sequence
<220> FEATURE:
<223> OTHER INFORMATION: Synthetic Construct

<400> SEQUENCE: 11
cagatccagt tggtacagtc tggacctgag ctgaagaagc ctggagagac agtcaagatc      60
tcctgcaagg cttctgggta taccttcaca gactatgcat ttagctgggt gaaacaggct     120
ccaggaaagg gtttaaagtg gatgggctgg ataaccacta acactggaga agccacatat     180
gctgatgact tcaagggacg gtttgccttc tctttggaaa cctctgccag cactgcctat     240
ttgcagatca gcaacctcaa aaatgaggac acggctacat atttctgtgc aagagagacg     300
gaatacggtg atagctcctg gtttgggcac tggggccaag ggactctggt cactgtctct     360
gcagctaaaa caacagcccc atcggtctat ccgctagccc ctgtgtgtgg agatacaact     420
ggctcctcgg tgactctagg atgcctggtc aagggttatt ccctgagcc agtgaccttg      480
```

-continued

```
acctggaact ctggcagcct gtccagtggt gtgcacacct tcccagctgt cctgcagtct      540
gacctctaca ccctcagcag ctcagtgact gtaacgtcga gcacctggcc cagccagtcc      600
atcacctgca atgtggccca cccggcaagc agcaccaagg tggacaagaa aattgagccc      660
agagggccca caatcaagcc ctgtcctcca tgcaaatgcc cagcacctaa cctcttgggt      720
ggaccatccg tcttcatctt ccctccaaag atcaaggatg tactcatgat ctccctgagc      780
cccatagtca catgtgtggt ggtggatgtg agcgaggatg acccagatgt ccagatcagc      840
tggtttgtga acaacgtgga agtacacaca gctcagacac aaacccatag agaggattac      900
aacagtactc tccgggtggt cagtgccctc cccatccagc accaggactg gatgagtggc      960
aaggagttca atgcaaggt caacaacaaa gacctcccag cgcccatcga gagaaccatc      1020
tcaaaaccca aagggtcagt aagagctcca caggtatatg tcttgcctcc accagaagaa      1080
gagatgacta agaaacaggt cactctgacc tgcatggtca cagacttcat gcctgaagac      1140
atttacgtgg agtggaccaa caacgggaaa acagagctaa actacaagaa cactgaacca      1200
gtcctggact ctgatggttc ttacttcatg tacagcaagc tgagagtgga aaagaagaac      1260
tgggtggaaa gaaatagcta ctcctgttca gtggtccacg agggtctgca caatcaccac      1320
acgactaaga gcttctcccg gactccgggt aaa      1353
```

```
<210> SEQ ID NO 12
<211> LENGTH: 654
<212> TYPE: DNA
<213> ORGANISM: Artificial Sequence
<220> FEATURE:
<223> OTHER INFORMATION: Synthetic Construct

<400> SEQUENCE: 12
gacattgtgc tgacccaatc tccagcttct ttggccgtgt ctctagggca gagggccacc       60
atatcctgca gagccagtga aagtgttgat ggatggggca atagtttcat gcactggtac      120
cagcagaaac caggacagcc acccaaactc ctcatctatc tcgctaccta tcgcgtagct      180
gggatccctg ccaggttcag tggcagtggg tctaggacag acttcaccct caccattaat      240
cctgtggagg ctgatgatgt tgcaacctat tattgtatgc agagtagtga agatccgtac      300
acgttcggag gggggaccaa gctggaaata aaacgggctg atgcggcgcc cactgtatcc      360
atcttcccac catccagtga gcagttaaca tctggaggtg ctagcgtcgt gtgcttcttg      420
aacaacttct accccaaaga catcaatgtc aagtggaaga ttgatggcag tgaacgacaa      480
aatggcgtcc tgaacagttg gactgatcag gacagcaaag acagcaccta cagcatgagc      540
agcaccctca cgttgaccaa ggacgagtat gaacgacata cagctatac ctgtgaggcc       600 actcacaaga tcacaacttc acccattgtc aagagcttca caggaatga gtgt      654
```

```
<210> SEQ ID NO 13
<211> LENGTH: 10
<212> TYPE: PRT
<213> ORGANISM: Artificial Sequence
<220> FEATURE:
<223> OTHER INFORMATION: Synthetic Construct

<400> SEQUENCE: 13

Gly Tyr Asn Phe Thr Asn Tyr Trp Leu His
1               5                   10
```

```
<210> SEQ ID NO 14
<211> LENGTH: 17
<212> TYPE: PRT
```

-continued

<213> ORGANISM: Artificial Sequence
<220> FEATURE:
<223> OTHER INFORMATION: Synthetic Construct

<400> SEQUENCE: 14

Glu Leu Asp Pro Glu Tyr Gly Phe Ala Asn Tyr Asn Gln Lys Phe Lys
1               5                   10                  15

Gly

<210> SEQ ID NO 15
<211> LENGTH: 5
<212> TYPE: PRT
<213> ORGANISM: Artificial Sequence
<220> FEATURE:
<223> OTHER INFORMATION: Synthetic Construct

<400> SEQUENCE: 15

Gly Phe Met Asp Tyr
1               5

<210> SEQ ID NO 16
<211> LENGTH: 16
<212> TYPE: PRT
<213> ORGANISM: Artificial Sequence
<220> FEATURE:
<223> OTHER INFORMATION: Synthetic Construct

<400> SEQUENCE: 16

Arg Ser Ser Arg Ser Leu Leu Asp Pro Asp Gly Lys Thr Tyr Leu Asn
1               5                   10                  15

<210> SEQ ID NO 17
<211> LENGTH: 7
<212> TYPE: PRT
<213> ORGANISM: Artificial Sequence
<220> FEATURE:
<223> OTHER INFORMATION: Synthetic Construct

<400> SEQUENCE: 17

Leu Val Ser Lys Leu Asp Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Construct

<400> SEQUENCE: 18

Trp Gln Gly Thr His Leu Pro Val Thr
1               5

<210> SEQ ID NO 19
<211> LENGTH: 114
<212> TYPE: PRT
<213> ORGANISM: Artificial Sequence
<220> FEATURE:
<223> OTHER INFORMATION: Synthetic Construct

<400> SEQUENCE: 19

Gln Val Gln Val Gln Gln Ser Gly Ala Glu Leu Val Met Pro Gly Thr
1               5                   10                  15

Ser Val Lys Leu Ser Cys Lys Ala Ser Gly Tyr Asn Phe Thr Asn Tyr
            20                  25                  30

```
Trp Leu His Trp Val Lys Gln Arg Pro Gly Gln Gly Leu Glu Trp Ile
        35                  40                  45

Gly Glu Leu Asp Pro Glu Tyr Gly Phe Ala Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ser Ala Gly Phe Met Asp Tyr Trp Gly Gln Gly Thr Ser Val Thr Val
            100                 105                 110

Ser Ser

<210> SEQ ID NO 20
<211> LENGTH: 112
<212> TYPE: PRT
<213> ORGANISM: Artificial Sequence
<220> FEATURE:
<223> OTHER INFORMATION: Synthetic Construct

<400> SEQUENCE: 20

Asp Val Val Met Thr Gln Thr Pro Leu Thr Leu Ser Val Asn Ile Gly
1               5                   10                  15

Gln Pro Ala Ser Ile Ser Cys Arg Ser Ser Arg Ser Leu Leu Asp Pro
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Arg Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Leu Pro Val Thr Phe Gly Gly Gly Thr Lys Leu Glu Ile Lys
            100                 105                 110

<210> SEQ ID NO 21
<211> LENGTH: 444
<212> TYPE: PRT
<213> ORGANISM: Artificial Sequence
<220> FEATURE:
<223> OTHER INFORMATION: Synthetic Construct

<400> SEQUENCE: 21

Gln Val Gln Val Gln Gln Ser Gly Ala Glu Leu Val Met Pro Gly Thr
1               5                   10                  15

Ser Val Lys Leu Ser Cys Lys Ala Ser Gly Tyr Asn Phe Thr Asn Tyr
            20                  25                  30

Trp Leu His Trp Val Lys Gln Arg Pro Gly Gln Gly Leu Glu Trp Ile
        35                  40                  45

Gly Glu Leu Asp Pro Glu Tyr Gly Phe Ala Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ser Ala Gly Phe Met Asp Tyr Trp Gly Gln Gly Thr Ser Val Thr Val
            100                 105                 110
```

-continued

```
Ser Ser Ala Lys Thr Thr Ala Pro Ser Val Tyr Pro Leu Ala Pro Val
        115                 120                 125

Cys Gly Asp Thr Thr Gly Ser Ser Val Thr Leu Gly Cys Leu Val Lys
        130                 135                 140

Gly Tyr Phe Pro Glu Pro Val Thr Leu Thr Trp Asn Ser Gly Ser Leu
145                 150                 155                 160

Ser Ser Gly Val His Thr Phe Pro Ala Val Leu Gln Ser Asp Leu Tyr
                165                 170                 175

Thr Leu Ser Ser Ser Val Thr Val Thr Ser Ser Thr Trp Pro Ser Gln
                180                 185                 190

Ser Ile Thr Cys Asn Val Ala His Pro Ala Ser Ser Thr Lys Val Asp
                195                 200                 205

Lys Lys Ile Glu Pro Arg Gly Pro Thr Ile Lys Pro Cys Pro Pro Cys
        210                 215                 220

Lys Cys Pro Ala Pro Asn Leu Leu Gly Gly Pro Ser Val Phe Ile Phe
225                 230                 235                 240

Pro Pro Lys Ile Lys Asp Val Leu Met Ile Ser Leu Ser Pro Ile Val
                245                 250                 255

Thr Cys Val Val Val Asp Val Ser Glu Asp Asp Pro Asp Val Gln Ile
                260                 265                 270

Ser Trp Phe Val Asn Asn Val Glu Val His Thr Ala Gln Thr Gln Thr
                275                 280                 285

His Arg Glu Asp Tyr Asn Ser Thr Leu Arg Val Val Ser Ala Leu Pro
        290                 295                 300

Ile Gln His Gln Asp Trp Met Ser Gly Lys Glu Phe Lys Cys Lys Val
305                 310                 315                 320

Asn Asn Lys Asp Leu Pro Ala Pro Ile Glu Arg Thr Ile Ser Lys Pro
                325                 330                 335

Lys Gly Ser Val Arg Ala Pro Gln Val Tyr Val Leu Pro Pro Pro Glu
                340                 345                 350

Glu Glu Met Thr Lys Lys Gln Val Thr Leu Thr Cys Met Val Thr Asp
                355                 360                 365

Phe Met Pro Glu Asp Ile Tyr Val Glu Trp Thr Asn Asn Gly Lys Thr
        370                 375                 380

Glu Leu Asn Tyr Lys Asn Thr Glu Pro Val Leu Asp Ser Asp Gly Ser
385                 390                 395                 400

Tyr Phe Met Tyr Ser Lys Leu Arg Val Glu Lys Lys Asn Trp Val Glu
                405                 410                 415

Arg Asn Ser Tyr Ser Cys Ser Val Val His Glu Gly Leu His Asn His
                420                 425                 430

His Thr Thr Lys Ser Phe Ser Arg Thr Pro Gly Lys
        435                 440
```

```
<210> SEQ ID NO 22
<211> LENGTH: 219
<212> TYPE: PRT
<213> ORGANISM: Artificial Sequence
<220> FEATURE:
<223> OTHER INFORMATION: Synthetic Construct

<400> SEQUENCE: 22

Asp Val Val Met Thr Gln Thr Pro Leu Thr Leu Ser Val Asn Ile Gly
1               5                   10                  15

Gln Pro Ala Ser Ile Ser Cys Arg Ser Ser Arg Ser Leu Leu Asp Pro
                20                  25                  30
```

-continued

```
Asp Gly Lys Thr Tyr Leu Asn Trp Leu Leu Gln Arg Pro Gly Gln Ser
        35                  40                  45
```

```
Pro Lys Arg Leu Ile Tyr Leu Val Ser Lys Leu Asp Ser Arg Val Pro
        50                  55                  60
```

```
Asp Arg Phe Thr Gly Ser Gly Ser Gly Thr Asp Phe Thr Leu Lys Ile
65                  70                  75                  80
```

```
Ser Arg Val Glu Ala Glu Asp Leu Gly Val Tyr Tyr Cys Trp Gln Gly
                85                  90                  95
```

```
Thr His Leu Pro Val Thr Phe Gly Gly Gly Thr Lys Leu Glu Ile Lys
            100                 105                 110
```

```
Arg Ala Asp Ala Ala Pro Thr Val Ser Ile Phe Pro Pro Ser Ser Glu
            115                 120                 125
```

```
Gln Leu Thr Ser Gly Gly Ala Ser Val Val Cys Phe Leu Asn Asn Phe
        130                 135                 140
```

```
Tyr Pro Lys Asp Ile Asn Val Lys Trp Lys Ile Asp Gly Ser Glu Arg
145                 150                 155                 160
```

```
Gln Asn Gly Val Leu Asn Ser Trp Thr Asp Gln Asp Ser Lys Asp Ser
                165                 170                 175
```

```
Thr Tyr Ser Met Ser Ser Thr Leu Thr Leu Thr Lys Asp Glu Tyr Glu
            180                 185                 190
```

```
Arg His Asn Ser Tyr Thr Cys Glu Ala Thr His Lys Thr Ser Thr Ser
            195                 200                 205
```

```
Pro Ile Val Lys Ser Phe Asn Arg Asn Glu Cys
    210                 215
```

```
<210> SEQ ID NO 23
<211> LENGTH: 1332
<212> TYPE: DNA
<213> ORGANISM: Artificial Sequence
<220> FEATURE:
<223> OTHER INFORMATION: Synthetic Construct

<400> SEQUENCE: 23
caggtccaag tgcagcagtc tggggctgag cttgtgatgc ctgggacttc agtgaagctg      60
tcctgcaagg cctctggcta taacttcact aattattggt tacactgggt gaagcagagg     120
cctggacaag gccttgagtg gatcggagag ctcgaccctg aatatggttt tgcgaactac     180
aatcaaaagt tcaagggcaa ggccacattg actgtagaca atcctccag cacagcctac      240 atgcagctca gcagcctgac atctgaggac tctgcggtct attactgttc tgccgggttc     300
atggactact ggggtcaagg aacctcagtc accgtctcct cagctaaaac aacagcccca     360
tcggtctatc cgctagcccc tgtgtgtgga gatacaactg gctcctcggt gactctagga     420
tgcctggtca aggttatttt ccctgagcca gtgaccttga cctggaactc tggcagcctg     480
tccagtggtg tgcacacctt cccagctgtc ctgcagtctg acctctacac cctcagcagc     540
tcagtgactg taacgtcgag cacctggccc agccagtcca tcacctgcaa tgtggcccac     600
ccggcaagca gcaccaaggt ggacaagaaa attgagccca gagggcccac aatcaagccc     660
tgtcctccat gcaaatgccc agcacctaac ctcttgggtg accatccgt cttcatcttc      720 cctccaaaga tcaaggatgt actcatgatc tccctgagcc ccatagtcac atgtgtggtg     780
gtggatgtga gcgaggatga cccagatgtc cagatcagct ggtttgtgaa caacgtggaa     840
gtacacacag ctcagacaca aacccataga gaggattaca acagtactct ccgggtggtc     900
agtgccctcc ccatccagca ccaggactgg atgagtggca ggagttcaa atgcaaggtc      960 aacaacaaag acctcccagc gcccatcgag agaaccatct caaaacccaa agggtcagta    1020
```
agagctccac aggtatatgt cttgcctcca ccagaagaag agatgactaa gaaacaggtc        1080
actctgacct gcatggtcac agacttcatg cctgaagaca tttacgtgga gtggaccaac        1140
aacgggaaaa cagagctaaa ctacaagaac actgaaccag tcctggactc tgatggttct        1200
tacttcatgt acagcaagct gagagtggaa aagaagaact gggtggaaag aaatagctac        1260
tcctgttcag tggtccacga gggtctgcac aatcaccaca cgactaagag cttctcccgg        1320
actccgggta aa                                                           1332

<210> SEQ ID NO 24
<211> LENGTH: 657
<212> TYPE: DNA
<213> ORGANISM: Artificial Sequence
<220> FEATURE:
<223> OTHER INFORMATION: Synthetic Construct

<400> SEQUENCE: 24
gatgttgtga tgacccagac tccactcact ttgtcggtta acattggaca accagcctcc         60
atctcttgca ggtcaagtcg gagcctctta gatccagatg gaaagacata tttgaattgg        120
ttgttacaga ggccaggcca gtctccaaag cgcctaatct atctggtgtc taaactggac        180
tctagagtcc ctgacaggtt cactggcagt ggatcaggga cagatttcac actgaaaatc        240
agcagagtgg aggctgagga tgtgggagtt tattattgct ggcaaggtac acatcttcct        300
gtaacgttcg gtggaggcac caagctggaa atcaaacggg ctgatgcggc gcccactgta        360
tccatcttcc caccatccag tgagcagtta acatctggag gtgctagcgt cgtgtgcttc        420
ttgaacaact ctaccccaa agacatcaat gtcaagtgga gagattgatgg cagtgaacga        480 caaaatggcg tcctgaacag ttggactgat caggacagca agacagcac ctacagcatg        540 agcagcaccc tcacgttgac caaggacgag tatgaacgac ataacagcta tacctgtgag        600
gccactcaca agacatcaac ttcacccatt gtcaagagct caacaggaa tgagtgt          657

<210> SEQ ID NO 25
<211> LENGTH: 37
<212> TYPE: PRT
<213> ORGANISM: Homo sapiens

<400> SEQUENCE: 25

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 26
<211> LENGTH: 35
<212> TYPE: PRT
<213> ORGANISM: Homo sapiens

<400> SEQUENCE: 26

Gln Gly Thr Phe Thr Ser Asp Tyr Ser Lys Tyr Leu Asp Ser Arg Arg
1               5                   10                  15

Ala Gln Asp Phe Val Gln Trp Leu Met Asn Thr Lys Arg Asn Arg Asn
            20                  25                  30

Asn Ile Ala
        35

-continued

```
<210> SEQ ID NO 27
<211> LENGTH: 34
<212> TYPE: PRT
<213> ORGANISM: Homo sapiens

<400> SEQUENCE: 27

Gly Thr Phe Thr Ser Asp Tyr Ser Lys Tyr Leu Asp Ser Arg Arg Ala
1               5                   10                  15

Gln Asp Phe Val Gln Trp Leu Met Asn Thr Lys Arg Asn Arg Asn Asn
            20                  25                  30

Ile Ala

<210> SEQ ID NO 28
<211> LENGTH: 69
<212> TYPE: PRT
<213> ORGANISM: Homo sapiens

<400> SEQUENCE: 28

Arg Ser Leu Gln Asp Thr Glu Glu Lys Ser Arg Ser Phe Ser Ala Ser
1               5                   10                  15

Gln Ala Asp Pro Leu Ser Asp Pro Asp Gln Met Asn Glu Asp Lys Arg
            20                  25                  30

His Ser Gln Gly Thr Phe Thr Ser Asp Tyr Ser Lys Tyr Leu Asp Ser
        35                  40                  45

Arg Arg Ala Gln Asp Phe Val Gln Trp Leu Met Asn Thr Lys Arg Asn
        50                  55                  60

Arg Asn Asn Ile Ala
65

<210> SEQ ID NO 29
<211> LENGTH: 41
<212> TYPE: PRT
<213> ORGANISM: Homo sapiens

<400> SEQUENCE: 29

Glu Asp Lys Arg His Ser Gln Gly Thr Phe Thr Ser Asp Tyr Ser Lys
1               5                   10                  15

Tyr Leu Asp Ser Arg Arg Ala Gln Asp Phe Val Gln Trp Leu Met Asn
            20                  25                  30

Thr Lys Arg Asn Arg Asn Asn Ile Ala
        35                  40

<210> SEQ ID NO 30
<211> LENGTH: 29
<212> TYPE: PRT
<213> ORGANISM: Homo sapiens

<400> SEQUENCE: 30

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 31
<211> LENGTH: 27
<212> TYPE: PRT
<213> ORGANISM: Homo sapiens

<400> SEQUENCE: 31

Gln Gly Thr Phe Thr Ser Asp Tyr Ser Lys Tyr Leu Asp Ser Arg Arg
```

-continued

```
1               5               10              15

Ala Gln Asp Phe Val Gln Trp Leu Met Asn Thr
                20              25

<210> SEQ ID NO 32
<211> LENGTH: 26
<212> TYPE: PRT
<213> ORGANISM: Homo sapiens

<400> SEQUENCE: 32

Gly Thr Phe Thr Ser Asp Tyr Ser Lys Tyr Leu Asp Ser Arg Arg Ala
1               5               10              15

Gln Asp Phe Val Gln Trp Leu Met Asn Thr
                20              25

<210> SEQ ID NO 33
<211> LENGTH: 42
<212> TYPE: PRT
<213> ORGANISM: Homo sapiens

<400> SEQUENCE: 33

Tyr Ala Glu Gly Thr Phe Ile Ser Asp Tyr Ser Ile Ala Met Asp Lys
1               5               10              15

Ile His Gln Gln Asp Phe Val Asn Trp Leu Leu Ala Gln Lys Gly Lys
                20              25              30

Lys Asn Asp Trp Lys His Asn Ile Thr Gln
        35              40

<210> SEQ ID NO 34
<211> LENGTH: 31
<212> TYPE: PRT
<213> ORGANISM: Homo sapiens

<400> SEQUENCE: 34

His Ala Glu Gly Thr Phe Thr Ser Asp Val Ser Ser Tyr Leu Glu Gly
1               5               10              15

Gln Ala Ala Lys Glu Phe Ile Ala Trp Leu Val Lys Gly Arg Gly
                20              25              30

<210> SEQ ID NO 35
<211> LENGTH: 29
<212> TYPE: PRT
<213> ORGANISM: Homo sapiens

<400> SEQUENCE: 35

Glu Gly Thr Phe Thr Ser Asp Val Ser Ser Tyr Leu Glu Gly Gln Ala
1               5               10              15

Ala Lys Glu Phe Ile Ala Trp Leu Val Lys Gly Arg Gly
                20              25

<210> SEQ ID NO 36
<211> LENGTH: 180
<212> TYPE: PRT
<213> ORGANISM: Homo sapiens

<400> SEQUENCE: 36

Met Lys Ser Ile Tyr Phe Val Ala Gly Leu Phe Val Met Leu Val Gln
1               5               10              15

Gly Ser Trp Gln Arg Ser Leu Gln Asp Thr Glu Glu Lys Ser Arg Ser
                20              25              30

Phe Ser Ala Ser Gln Ala Asp Pro Leu Ser Asp Pro Asp Gln Met Asn
```

-continued

```
              35                    40                    45

Glu Asp Lys Arg His Ser Gln Gly Thr Phe Thr Ser Asp Tyr Ser Lys
    50                    55                    60

Tyr Leu Asp Ser Arg Arg Ala Gln Asp Phe Val Gln Trp Leu Met Asn
65                    70                    75                    80

Thr Lys Arg Asn Arg Asn Asn Ile Ala Lys Arg His Asp Glu Phe Glu
                  85                    90                    95

Arg His Ala Glu Gly Thr Phe Thr Ser Asp Val Ser Ser Tyr Leu Glu
                  100                   105                   110

Gly Gln Ala Ala Lys Glu Phe Ile Ala Trp Leu Val Lys Gly Arg Gly
              115                   120                   125

Arg Arg Asp Phe Pro Glu Glu Val Ala Ile Val Glu Glu Leu Gly Arg
    130                   135                   140

Arg His Ala Asp Gly Ser Phe Ser Asp Glu Met Asn Thr Ile Leu Asp
145                   150                   155                   160

Asn Leu Ala Ala Arg Asp Phe Ile Asn Trp Leu Ile Gln Thr Lys Ile
              165                   170                   175

Thr Asp Arg Lys
              180
```